US008877748B2

(12) United States Patent
Huang et al.

(10) Patent No.: US 8,877,748 B2
(45) Date of Patent: Nov. 4, 2014

(54) HETEROCYCLIC FUSED ANTHRAQUINONE DERIVATIVES, MANUFACTURING METHOD AND PHARMACEUTICAL COMPOSITION USING THEREOF

(71) Applicant: National Defense Medical Center, Taipei (TW)

(72) Inventors: Hsu-Shan Huang, Taipei (TW); Yu-Ru Lee, Taipei (TW); Tsung-Chih Chen, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 13/782,327

(22) Filed: Mar. 1, 2013

(65) Prior Publication Data

US 2013/0289028 A1 Oct. 31, 2013

(30) Foreign Application Priority Data

Apr. 27, 2012 (TW) .............................. 101115193 A

(51) Int. Cl.
*C07D 417/12* (2006.01)
*C07D 285/14* (2006.01)
*A61K 31/4245* (2006.01)

(52) U.S. Cl.
CPC ................... *C07D 417/12* (2013.01); *C07D 285/14* (2013.01)
USPC ...................... 514/228.5; 514/362; 514/232.8; 514/338; 544/134; 544/58.7; 546/268.7; 548/126

(58) Field of Classification Search
CPC .. C07D 417/10; C07D 417/12; C07D 285/14; A61K 31/5377; A61K 31/496; A61K 31/433
USPC ............ 514/228.5, 232.8, 338, 362; 544/134, 544/58.7; 546/268.7; 548/126
See application file for complete search history.

(56) References Cited

U.S. PATENT DOCUMENTS

2009/0253707 A1 * 10/2009 Huang ........................... 514/250

OTHER PUBLICATIONS

Gorelik et al. "Reaction of Antra[1,2-c]-1,2,5-thiadiazole-6,11-dione with Nucleophilic Agents" in Chemistry of Heterocyclic Compounds. Studies on Quinones. 1968, 4, 337-341 (Russian Original: Khimiya Geterotsiklicheskikh Soedinenii 1968, (3), 453-8).*
Dong et al. "Selection of Evodiamine as a Novel Topoisomerase I Inhibitor by Structure-Based Virtual Screening and Hit Optimization of Evodiamine Derivatives as Antitumor Agents" J. Med. Chem. 2010, 53, 7521-31.*
Gorelik et al. "Reaction of Antra[1,2-c]-1,2,5-thiadiazole-6,11-dione with Nucleophilic Agents" in Chemistry of Heterocyclic Compounds. Studies on Quinones. 1968, 4, 337-341 (Russian Original: Khimiya Geterotsiklicheskikh Soedinenii 1968, 4(3), 453-8).*
Gorelik et al. Zh. Org. Khimii 1971, 7(5), 1044-9.*
Gorelik et al. "Studies on Quinones. V. Anthra[1,2-c]-1,2,5-thiadiazole-6,11-diones and Their Reaction with Amines" Khimiya Geterotsiklicheskikh Soedinenii (1968), 4(3), 447-452.*

* cited by examiner

*Primary Examiner* — Samantha Shterengarts
*Assistant Examiner* — Amanda L Aguirre
(74) *Attorney, Agent, or Firm* — Muncy, Geissler, Olds & Lowe, P.C.

(57) ABSTRACT

A heterocyclic fused anthraquinone derivative, which is represented by a formula (I):

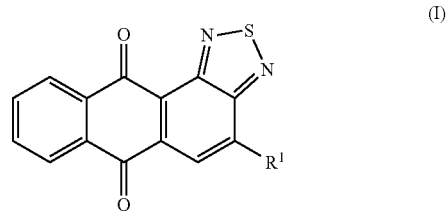

wherein $R^1$ is a substituent being one selected from a group consisting of hydrogen, halogens, aminoalkyl group, sulfoalkyl group, haloalkyl group, piperazino group, sulfonyl group, morpholino group, alkali group or one substituent represented by a formula (II):

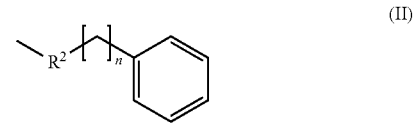

wherein $R^2$ is amino group, oxyl group or a thiol group. In the meantime, a method for manufacturing the above-mentioned heterocyclic fused anthraquinone derivatives and a pharmaceutical composition using thereof are also disclosed here.

12 Claims, 1 Drawing Sheet

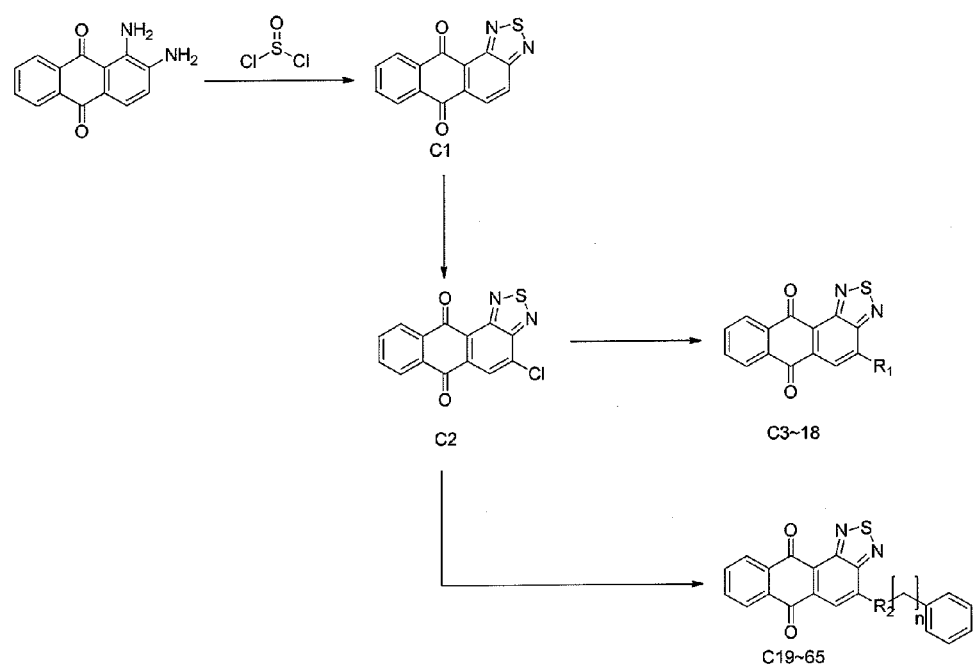

HETEROCYCLIC FUSED ANTHRAQUINONE DERIVATIVES, MANUFACTURING METHOD AND PHARMACEUTICAL COMPOSITION USING THEREOF

CROSS-REFERENCE TO RELATED APPLICATIONS

This Non-provisional application claims priority under 35 U.S.C. §119(a) on Patent Application No(s). 101115193 filed in Taiwan, Republic of China Apr. 27, 2012, the entire contents of which are hereby incorporated by reference.

FIELD OF THE INVENTION

The present invention is related to heterocyclic fused anthraquinone derivatives, especially related to heterocyclic fused anthraquinone derivatives for treating cancer and the preparation method thereof, and the pharmaceutical composition comprising the heterocyclic fused anthraquinone derivatives.

BACKGROUND OF THE INVENTION

Cancer is mainly due to the abnormal cell lesions or cells with abnormal proliferation. The assembled formation of lumps, we called them Tumor. Tumor can be simply classified into benign and malignant. Generally, benign tumors whose growth is relatively slow, and does not affect the adjacent normal tissue, the risk is non-fatal. However, if benign tumor is formed on the vital parts of the body, surgery can often excise without recurrence. Malignant tumor is more commonly known as "cancer". Proliferations of cancer cells can not only assemble into amass but also locally invade surrounding tissue and transfer to other part of the body through the circulatory system or the lymphatic system. Therefore, if the cancer is not treated properly, it may lead to death. In recent years, the incidence of cancer rise sustainably which treatment is becoming more important.

Generally, the treatment of cancer can be categorized into three types: surgery, radiation therapy and chemotherapy. Due to the different location of the tumor, and the degree of development of the patient's physical condition, many new experimental therapies have been developed in recent years. For example: gene therapy, molecular targeted therapies, and angiogenic therapy.

In addition, in most organisms, replication and maintenance of telomere length of the ends of chromosomes rely on telomerase. Many studies have pointed out that telomerase is only active in some of the high proliferative capacity cells in human body for example, germ cell, hematopoietic cells, stem cells, immortalized cell and most of the tumor cells. In contrast, normal somatic does not have telomerase activity, so telomeres is gradually shortened with increasing number of cell division, when the telomere is shorter to a certain degree, the cells will stop dividing into the aging phase, eventually dying, this period is called M1 (mortality stage 1).

In M1, if inhibit tumor cells (tumor suppressor gene) gene mutates, such as p53 and Rb, which will stop the aging cells stage and continue cell division, this period is called M2 (mortality stage 2). In this period, telomere length will still shorten due to the non-existence of telomerase activity. Telomeres will not be able to protect the integrity of the ends of chromosomes which lead to chromosomal instability phenomenon. The cells cannot complete the genetic message passing and gradually die. Thus, the M2 period is also known as the crisis period. Most of the cells will die in the M2 period, only a few cells survive due to the telomerase activity, these unrestricted cells are divided continuously and becoming the immortality cells (or cancer cells).

Due to the fact that most normal cells with the telomerase activity did not even exist, and vice versa in almost all human tumor cells has active telomerase, telomerase research in targeted therapy has become many emerging target for the drug target treatment.

Rapid growth or excessive proliferation of cells, due to the need to conduct DNA transcription and translation, the supercoiled structure relative essential often unlock and wound, and therefore is responsible for this aspect of the enzyme—topoisomerases considered a target goal of treatment; mainly use when DNA wraps untie the broken part, so that it can no longer be joined together, to inhibition of rapidly dividing cells, such as cancer cells. For the inhibition of topoisomerase mechanisms, there are basically three forms, a first: Drug first engagement with the DNA fragment, followed by topoisomerase II is bonded to the composite body formed by the drugs and DNA; second: topoisomerase II first engagement with the DNA fragment, and then the drug in combination with topoisomerase II and DNA complexes; last one: the drugs will first engage on topoisomerase II, followed by the complex formed realized with the DNA fragment engaging. Comprehensive three paths, and finally are topoisomerase drugs and DNA fragments will form four complex configuration (ternary complex); while the main mechanism of this effect, by the start of double-stranded DNA topoisomerase role cut off, then the complex topology of the enzyme with drugs stay in the DNA, because the DNA is cut not pick, so when copy conduct this point, will be due to the fracture leaving the enzyme can not be the role of cells discriminant for DNA breakage of leading to cell death.

Overall, the anthracycline cytotoxic has pleiotropic effect, and the inhibition of cell growth seems to be very specific, meaning many drugs such as daunorubicin, doxorubicin and other anthracycline have been widely used as anticancer drugs. However, their clinical uses are limited because of their strong cardiotoxicity tolerance.

Furthermore, the application of first-generation of anthracycline such as doxorubicin and daunorubicin, is like a double-edged sword-like, however, some tumor disease can only be treated by these drugs. After long-term administration, the cardiotoxicity and heart failure is induced. Then, the second-generation of anthracycline such as Epirubicin, Ida neomycin have improved the therapeutic index, but the treatment induced cardiomyopathy crisis have not been eliminated.

SUMMARY OF THE INVENTION

Accordingly, the present invention is to provide a non-nucleoside telomerase inhibitor, try to develop a more effective cancer-treating enzyme inhibitor by modifying the compounds structure. Anthraquinone derivative is a potential Topoisomerase inhibitor. The inventors investigate the different enzyme inhibitor and find the derivative show higher anti-cancer activity when cyclic anthraquinone fused with heterocyclic or form a heterocyclic structure, which trigger different mechanism in cancer cell. Tumor cells lead to over-expression of P-glycoprotein in multiple drug tolerance, which is related to the structure of anti-cancer drugs. The heterocyclic derivatives can significantly increase the accumulation of doxorubicin via multiple drug tolerance cells inhibit P-glycoprotein performance. Reversible mechanism of these multi-drug tolerance cells is based on the inhibition of P-glycoprotein function and increase the accumulation of anticancer drugs. Therefore, the tolerability of multiple drug tolerance the cytotoxic and multiple drugs tune variable combination of treatments can be used as the clinical treatment of multi-drug tolerance strategy.

Specifically, the present invention provides a heterocyclic fused anthraquinone derivatives, which is represented by a formula (I):

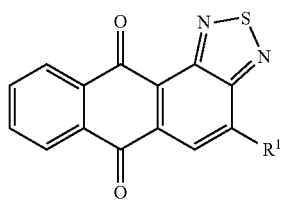

(I)

wherein $R^1$ is hydrogen, halogens, aminoalkyl group, sulfoalkyl group, haloalkyl group, piperazino group, sulfonyl group, morpholino group, alkali group or one substituent represented by a formula (II):

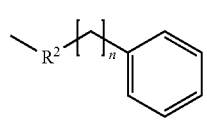

(II)

wherein $R^2$ is amino group, oxyl group or a thiol group, and the partial hydrogen of phenyl group represented by a formula (II) can be substituted by halogen, alkoxy group, nitro group, methylthio group or sulfhydryl, In one embodiment of the present invention, wherein $R^1$ is aminoalkyl group, sulfoalkyl group or haloalkyl group, the alkyl group can be selected from the group consisting of $C_{1-10}$ straight-chain alkyl group, $C_{3-10}$ branched alkyl group and $C_{3-10}$ cyclic alkyl group, and the halogens can be selected from the group consisting of F, Cl, Br and I.

In one embodiment of the present invention, wherein $R^1$ is Cl, sulfonic acid sodium, oxide potassium, diethylamino group, amino-propyl group, amino-cyclobutyl group, aminodimethyl group, amino-ethyl group, ethyl piperazino group, amino-cyclopentylamino group, amino-butylamino group, amino-ethylamino, amino-2-methylpropylamino group, thio-morpholino group, thio-ethyl group, thio-n-propyl group or thio-isopropyl group.

In one embodiment of the present invention, wherein the $R^2$ is amino group and the $R^1$ is 3-chlorophenylamino group, 2-methylphenylamino group, 3-methylphenylamino group, 4-methylphenylamino group, 4-chlorophenylamino group or 4-chloro-2-fluorophenylamino group.

In one embodiment of the present invention, wherein the $R^2$ is oxygen and $R^1$ is para-methylphenyl-oxy group.

In one embodiment of the present invention, wherein the $R^2$ is sulfur group and $R^1$ is phenylthio, 2,5-dimethylphenylthio group, benzylthio group, 4-chlorophenylthio group, 2-methylphenylthio group, 4-bromophenylthio group, 2,4-dimethylphenylthio group, 4-isopropylphenylthio group, 2-bromophenylthio group, 4-fluorophenylthio group, phenylthioethyl group, 2,3-dichlorophenylthio group, 4-tert-butylphenylthio group, 2-chlorophenylthio group, 2-fluorophenylthio group, 2,4,5-trichlorophenylthio group, 2,5-dichlorophenylthio group, 2-thiolphenylthio, 3-chlorophenylthio, 3-fluorophenylthio group, 2,4-difluorophenylthio group, 3-bromophenylthio group, 4-methoxyphenylthio group, 3,4-dimethylphenylthio group, 4-methylthiophenylthio group, 4-methylphenylthio group, 4-nitrophenylthio group, 3-methoxyphenylthio group, meta-benzylthio group, ortho-benzylthio group, 3,5-dimethylphenylthio group, 3-ethoxyphenylthio group, 2-ethylphenylthio group, 2-isopropylphenylthio group, 4-ethylphenylthio group, 2,6-diethylphenylthio group, 4-chlorobenzylthio group, 4-tert-butyl benzylthio group or pyridyl-2-thio group.

Another purpose of the present invention is to provide a method for preparation of the heterocyclic fused anthraquinone derivatives of claim 1, which steps as follows: 1,2-diaminoanthraquinone is reacted with thionyl chloride then by triethylamine to form a first product: 4-(phenethylthio)anthra[2,1-c][1,2,5]thiadiazole-6,11-dione; The first product is reacted with a halogen-comprising compound to form a second compound: 4-chloroanthraquinone[2,1-c][1,2,5]thiadiazole-6,11-dione; The second compound is solved in a N,N'-dicyclohexylcarbodiimide and tetrahydrofuran solution or ethylene glycol to form a mixed solution; A aminoalkyl group, sulfoalkyl group, haloalkyl group, piperazino group, sulfonyl group, morpholino group, alkali group or one substituent represented by a formula (II) —comprising compound is added in the mixed solution:

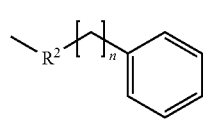

(II)

wherein $R^2$ is amino group, oxyl group or a thiol group, and the partial hydrogen of benzene in formula (II) can be substituted by halogen, alkoxy group, nitro group, methylthio group or sulfhydryl group; Stir the mixed solution; then filter and precipitate the mixed solution.

In one embodiment of the present invention, wherein the first product is aquinone [2,1-c][1,2,5]thiadiazole-6,11-dione, and halogen-comprising compound is KCl, where the second product is 4-chloroanthraquinone[2,1-c][1,2,5]thiadiazole-6,11-dione.

One more purpose of the present invention is to provide a pharmaceutical composition for treating cancer, which comprises a thiazole fused anthraquinone derivatives and the pharmaceutical acceptable salt and carrier thereof:

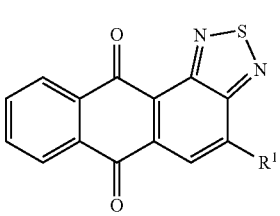

(I)

wherein $R^1$ is hydrogen, halogens, aminoalkyl group, sulfoalkyl group, haloalkyl group, piperazino group, sulfonyl group, morpholino group, alkali group or one substituent represented by a formula (II):

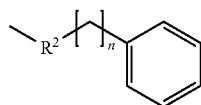

wherein R² is amino group, oxyl group or a thiol group, and the partial hydrogen of benzene in formula (II) can be substituted by halogen, alkoxy group, nitro group, methylthio group or sulfhydryl.

In one embodiment of the present invention, wherein R¹ is Cl, sulfonic acid sodium, oxide potassium, diethylamino group, amino-propyl group, amino-cyclobutyl group, amino-dimethyl group, amino-ethyl group, ethyl piperazino group, amimo-cyclopentylamino group, amino-butylamino group, amino-ethylamino, amino-2-methylpropylamino group, thio-morpholino group, thio-ethyl group, thio-n-propyl groupor thio-isopropyl group.

In one embodiment of the present invention, wherein the R² is amino group and the R¹ is 3-chlorophenylamino group, 2-methylphenylamino group, 3-methylphenylamino group, 4-methylphenylamino group, 4-chlorophenylamino group or 4-chloro-2-fluorophenylamino group.

In one embodiment of the present invention, wherein the R² is oxygen and R¹ is para-methylphenyl-oxy group.

In one embodiment of the present invention, wherein the R² is sulfur group and R¹ is phenylthio, 2,5-dimethylphenylthio group, benzylthio group, 4-chlorophenylthio group, 2-methylphenylthio group, 4-bromophenylthio group, 2,4-dimethylphenylthio group, 4-isopropylphenylthio group, 2-bromophenylthio group, 4-fluorophenylthio group, phenylthioethyl group, 2,3-dichlorophenylthio group, 4-tert-butylphenylthio group, 2-chlorophenylthio group, 2-fluorophenylthio group, 2,4,5-trichlorophenylthio group, 2,5-dichlorophenylthio group, 2-thiolphenylthio, 3-chlorophenylthio, 3-fluorophenylthio group, 2,4-difluorophenylthio group, 3-bromophenylthio group, 4-methoxyphenylthio group, 3,4-dimethylphenylthio group, 4-methylthiophenylthio group, 4-methylphenylthio group, 4-nitrophenylthio group, 3-methoxyphenylthio group, meta-benzylthio group, ortho-benzylthio group, 3,5-dimethylphenylthio group, 3-ethoxyphenylthio group, 2-ethylphenylthio group, 2-isopropylphenylthio group, 4-ethylphenylthio group, 2,6-diethylphenylthio group, 4-chlorobenzylthio group, 4-tert-butyl benzylthio group or pyridyl-2-thio group.

In one embodiment of the present invention, wherein the pharmaceutical acceptable salt is inorganic acid or organic acid or base physiological acceptable salt, the inorganic acid can be selected from the group consisting of HCl, HBr, H₂SO₄, sulfonic acid and H₂PO₃, wherein the organic salt can be selected from the group consisting of citric acid, acetic acid, maleic acid, fumaric acid, gluconic acid, glycolic acid, methanesulfonic acid, succinic acid and galactose.

In one embodiment of the present invention, wherein the carrier is excipient agent, diluting agent, thickening agent, bulking agent, binder, disintegrating agent, lubricating agent, oil or non-oil based agent, surfactant, suspending agent, gelating agent, supporting agent, preservative agent, antioxidative agent, stabilizing agent, coloring agent or fragrance.

In one embodiment of the present invention, wherein the excipient agent includes microcrystalline cellulose, polyvinylpyrrolidone, corn starch, modified starch, carboxymethyl stach sodium, polystyrenre, gelatinized starch, sugar, polyethylene glycol, polyvinyl alcohol, hypromellose, carboxymethyl cellulose, hydroxymethylcellulose or hydroxypropyl methylcellulose.

One embodiment of the present invention is used as a pharmaceutical composition inhibiting a non-adenosine telomerase.

One embodiment of the present invention is a powder, a granule, a liquid, a gel or a paste.

One embodiment of the present invention is transported by oral intake, epidermal absorption, injection or inhalation.

BRIEF DESCRIPTION OF THE DRAWINGS

FIG. 1 illustrates the preparation flow chart of compounds C1~C65.

DETAILED DESCRIPTION OF THE INVENTION

The present invention provides a the present invention provides a heterocyclic fused anthraquinone derivatives, which is represented by a formula (I):

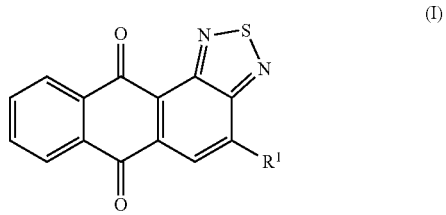

wherein R¹ is hydrogen, halogens, aminoalkyl group, sulfoalkyl group, haloalkyl group, piperazino group, sulfonyl group, morpholino group or alkali group.

Further, when R¹ is aminoalkyl group, sulfoalkyl group or haloalkyl group, the alkyl group can be selected from the group consisting of C₁₋₁₀ straight-chain alkyl group, C₃₋₁₀ branched alkyl group and C₃₋₁₀ cyclic alkyl group, and the halogens can be selected from the group consisting of F, Cl, Br and I.

That is, R¹ can be a methyl group, ethyl group, n-propyl group, iso-propyl group, n-butyl group, iso-butyl group, 2-butyl group, tert-butyl group, n-pentyl, iso-pentyl, tert-pentyl, neo-pentyl, n-hexyl, iso-hexyl, tert-hexyl, neo-hexyl, n-heptyl, iso-heptyl, tert-heptyl, n-octyl, tert-octyl, aminomethyl, aminoethyl, aminopropyl, thiomethyl, thioethyl, thiopropyl, fluoromethyl, fluoroethyl, fluoropropyl, chloromethyl, chloroethyl, chloropropyl, bormomethyl, bromoethyl, bromopropyl, iodomethyl, iodoethyl or iodopropyl.

Preferably, R¹ is, but not limited to, H, Cl, sulfonic acid sodium, oxide potassium, diethylamino group, amino-propyl group, amino-cyclobutyl group, amino-dimethyl group, amino-ethyl group, ethyl piperazino group, amimo-cyclopentylamino group, amino-butylamino group, amino-ethylamino, amino-2-methylpropylamino group, thio-morpholino group, thio-ethyl group, thio-n-propyl group or thio-isopropyl group.

Further, R¹ also can be a substitute represented by formula (II):

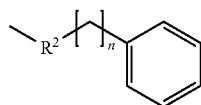 (II)

wherein R² is amino group, oxyl group or a thiol group, and the partial hydrogen of benzene in formula II can be substituted by halogen, alkoxy group, nitro group, methylthio group or sulfhydryl. Meanwhile, there is a carbon bond between R² and benzene in heterocyclic fused anthraquinone derivatives, which features as the longer branched chain to increase the activity of the enzyme by reacting more deeply. Besides, there is a benzene in the terminal end, which helps the localization of this compound on the active site of the enzyme to elongate the reacting period.

Furthermore, the alkoxy group can be, but not limited to a methoxy group, ethoxy group, n-propyoxy group or iso-propyoxy group.

In addition, in the preferred embodiment, when R² is amino group, R¹ is 3-chlorophenylamino group, 2-methylphenylamino group, 3-methylphenylamino group, 4-methylphenyl group, 4-chloro-phenylamino group or 4-chloro-2-fluorophenyl amine group.

In the preferred embodiment, when R² is O, R¹ can be a methylphenyl group.

In the preferred embodiment, when R² is a thio group, R¹ can be phenylthio group, 2,5-dimethyl-phenylthio group, benzylthio group, 4-chlorophenyl sulfur substituting group, 2-methoxyphenylthio group, 4-bromophenylthio group, 2,4-dimethylphenylthio group, 4-isopropylphenylthio group, 2-bromo-phenylthio group, 4-fluorophenylthio group, phenylthio group, 2,3-dichlorophenylthio group, 4-tert-alkylphenyl thio group, 2-chlorophenylthio group, 2-fluorophenylthio group, 2,4,5-trichlorophenylthio group, 2,5-dichlorophenylthio group, 2-phenylthio group, mercapto group, 3-chlorophenylthio group, 3-fluorophenylthio group, 2,4-difluorophenylthio group, 3-bromophenylthio group, 4-methoxyphenylthio group, 3,4-dimethoxyphenylthio group, 4-(methylthio)phenylthio group, 4-methylphenylthio group, 4-nitrophenylthio group, 3-methoxyphenylthio group, m-(phenylmethyl)thio group, o-(phenylmethyl)thio group, 3,5-dimethylphenylthio group, 3-ethoxybenzene group, 2-ethylphenylthio, 2-isopropylphenylthio group, 4-2-chlorobenzylthio group, 4-ethylphenylthio group, 2,6-dimethylphenylthio group, 4-chlorobenzylthio group, 4-tert-butylbenzylylthio group or a pyridyl-2 group.

Accordingly, the present invention provides a series of thiazole oxadiazol fusion anthraquinone derivatives as Table 1. The R¹ of C1~C65 in the preferred embodiment 65 compounds are listed in Table I of the invention. Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

Thiadiazole fusion anthraquinone derivatives C1~C65

| NO. | IUPAC Name | R¹ structure |
|---|---|---|
| C1 | Anthraquinone[2,1-c][1,2,5]thiadiazol-6,11-dione | H |
| C2 | 4-Chloro-anthraquinone[2,1-c][1,2,5]thiadiazole-6,11-dione | Cl |
| C3 | Sodium 6,11-dioxo-6,11-dihydroanthra[2,1-c][1,2,5]thiadiazole-4-sulfonate | —SO₂ONa |
| C4 | Potassium 6,11-dioxo-6,11-dihydroanthra[2,1-c][1,2,5]thiadiazol-4-olate | —OK |
| C5 | 4-(diethylamino)anthra[2,1-c][1,2,5]thiadiazol-6,11-dione | |
| C6 | 4-(propylamino)anthra-[2,1-c][1,2,5]thiadiazol-6,11-dione | |
| C7 | 4-(pyrrolidine-1-yl)anthra-[2,1-c][1,2,5]thiadiazol-6,11-dione | |
| C8 | 4-(2-dimethylamino)ethyl)amino)anthra[2,1-c][1,2,5]thiadiazol-6,11-dione | |
| C9 | 4-(4-ethyl-piperazin-1-yl)anthra[2,1-c][1,2,5]thiadiazol-6,11-dione | |

TABLE 1-continued

Thiadiazole fusion anthraquinone derivatives C1~C65

| NO. | IUPAC Name | R¹ structure |
|---|---|---|
| C10 | 4-morpholino-anthra[2,1-c][1,2,5]thiadiazol-6,11-dione |  |
| C11 | 4-(piperidine-1-yl)anthra[2,1-c][1,2,5]thiadiazol-6,11-dione | 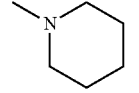 |
| C12 | 4-butylamino-anthra[2,1-c][1,2,5]thiadiazol-6,11-dione | 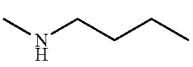 |
| C13 | 4-ethylamino anthra[2,1-c][1,2,5]thiadiazol-6,11-dione | 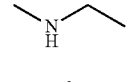 |
| C14 | 4-(isobutylamino)anthra[2,1-c][1,2,5]thiadiazol-6,11-dione-anthraquinone |  |
| C15 | 4-(thiomorpholino)anthra[2,1-c][1,2,5]thiadiazol-6,11-dione | 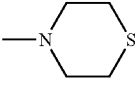 |
| C16 | 4-(ethylthio)anthra[2,1-c][1,2,5]thiadiazol-6,11-dione |  |
| C17 | 4-(n-propylthio)-anthra[2,1-c][1,2,5]thiadiazol-6,11-dione |  |
| C18 | 4-(isopropylthio)anthra[2,1-c][1,2,5]thiadiazol-6,11-dione | 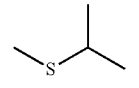 |
| C19 | 4-(phenylthio)anthra[2,1-c][1,2,5]thiadiazol-6,11-dione | 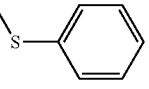 |
| C20 | 4-(2,5-dimethyl-phenyl-thio)anthra[2,1-c][1,2,5]thiadiazol-6,11-dione | 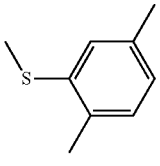 |
| C21 | 4-(benzyl-thio)anthra[2,1-c][1,2,5]thiadiazol-6,11-dione | 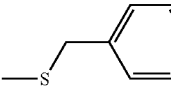 |
| C22 | 4-(4-chloro-phenylthio)anthra[2,1-c][1,2,5]thiadiazol-6,11-dione | 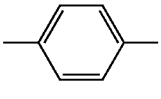 |
| C23 | 4-(2-methoxy-phenyl-thio)anthra[2,1-c][1,2,5]thiadiazol-6,11-dione | 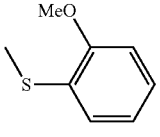 |
| C24 | 4-(4-bromo-phenyl-thio)anthra[2,1-c][1,2,5]thiadiazol-6,11-dione | 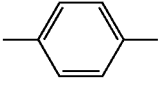 |

TABLE 1-continued

Thiadiazole fusion anthraquinone derivatives C1~C65

| NO. | IUPAC Name | R¹ structure |
|---|---|---|
| C25 | 4-(2,4-dimethylphenyl thio)anthra[2,1-c][1,2,5]thiadiazol-6,11-dione | 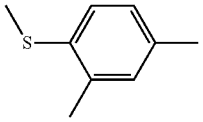 |
| C26 | 4-(4-isopropyl-phenyl-thio)anthra[2,1-c][1,2,5]thiadiazol-6,11-dione | 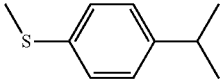 |
| C27 | 4-(2-bromo-phenyl thio)anthra[2,1-c][1,2,5]thiadiazol oxazole-6,11-dione | 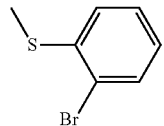 |
| C28 | 4-(4-fluoro-phenyl-thio)anthra[2,1-c][1,2,5]thiadiazol-6,11-dione | 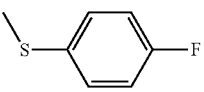 |
| C29 | 4-(phenethylthiol)anthra[2,1-c][1,2,5]thiadiazol-6,11-dione | 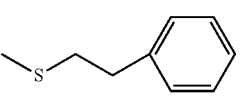 |
| C30 | 4-(2,3-dichloro-phenyl thio)anthra[2,1-c][1,2,5]thiadiazol oxazole-6,11-dione | 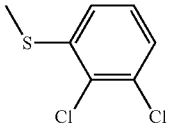 |
| C31 | 4-(4-tert-butyl-alkylphenyl-thio)anthra[2,1-c][1,2,5]thiadiazol-6,11-dione | 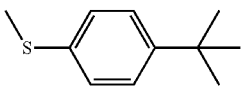 |
| C32 | 4-(2-chloro-phenyl thio)anthra[2,1-c][1,2,5]thiadiazol-6,11-dione | 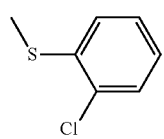 |
| C33 | 4-(2-fluoro-phenyl thio)anthra[2,1-c][1,2,5]thiadiazol oxazole-6,11-dione | 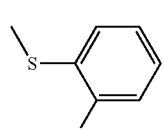 |
| C34 | 4-(2,4,5-trichloro-phenyl thio)anthra[2,1-C][1,2,5]thiadiazol-6,11-dione | 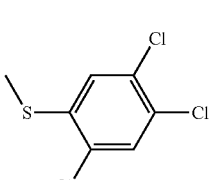 |
| C35 | 4-(2,5-dichloro-phenyl thio)anthra[2,1-c][1,2,5]thiadiazol oxazole-6,11-dione | 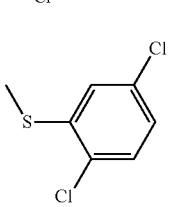 |

TABLE 1-continued

Thiadiazole fusion anthraquinone derivatives C1~C65

| NO. | IUPAC Name | R¹ structure |
|---|---|---|
| C36 | 4-(2-mercapto-phenyl-thio)anthra[2,1-c][1,2,5]thiadiazol oxazole-6,11-dione | 2-mercaptophenylthio group |
| C37 | 4-(3-chlorophenyl-thio)anthra[2,1-c][1,2,5]thiadiazol-6,11-dione | 3-chlorophenylthio group |
| C38 | 4-(3-fluorophenyl thio)anthra[2,1-c][1,2,5]thiadiazol-6,11-dione | 3-fluorophenylthio group |
| C39 | 4-(2,4-di fluorophenyl thio)anthra[2,1-c][1,2,5]thiadiazol-6,11-dione | 2,4-difluorophenylthio group |
| C40 | 4-(3-bromophenyl thio)anthra[2,1-c][1,2,5]thiadiazol-6,11-dione | 3-bromophenylthio group |
| C41 | 4-(4-methoxy-phenyl-thio)anthra[2,1-c][1,2,5]thiadiazol-6,11-dione | 4-methoxyphenylthio group |
| C42 | 4-(3,4-dimethoxy-phenyl-thio)anthra[2,1-c][1,2,5]thiadiazol-6,11-dione | 3,4-dimethoxyphenylthio group |
| C43 | 4-(4-(methylthio)phenyl thio)anthra[2,1-c][1,2,5]thiadiazol-6,11-dione | 4-(methylthio)phenylthio group (SCH₃) |
| C44 | 4-(4-methyl-phenyl-thio)anthra[2,1-c][1,2,5]thiadiazol-6,11-dione | 4-methylphenylthio group |
| C45 | 4-(4-nitrophenyl thio)anthra[2,1-c][1,2,5]thiadiazol oxazole-6,11-dione | 4-nitrophenylthio group (NO₂) |
| C46 | 4-(3-methoxy-phenyl-thio)anthra[2,1-c][1,2,5]thiadiazol-6,11-dione | 3-methoxyphenylthio group |
| C47 | 4-(m-phenyl methyl thio)anthra[2,1-c][1,2,5]thiadiazol-6,11-dione | m-methylphenylthio group |

TABLE 1-continued

Thiadiazole fusion anthraquinone derivatives C1~C65

| NO. | IUPAC Name |
|---|---|
| C48 | 4-(o-phenylmethyl thio)anthra[2,1-c][1,2,5]thiadiazol-6,11-dione |
| C49 | 4-(3,5-dimethyl-phenyl-thio)anthra[2,1-c][1,2,5]thiadiazol-6,11-dione |
| C50 | 4-(3-ethoxy-phenylthio)anthra[2,1-c][1,2,5]thiadiazol-6,11-dione |
| C51 | 4-(2-ethyl-phenylthio)anthra[2,1-c][1,2,5]thiadiazol-6,11-dione |
| C52 | 4-(2-isopropyl-phenyl-thio)anthra[2,1-c][1,2,5]thiadiazol-6,11-dione |
| C53 | 4-(2-chloro-benzyl thio)anthra[2,1-C][1,2,5]thiadiazol-6,11-dione |
| C54 | 4-(4-ethyl-phenyl-thio)anthra[2,1-c][1,2,5]thiadiazol oxazole-6,11-dione |
| C55 | 4-(2,6-dimethylphenyl thio)anthra[2,1-c][1,2,5]thiadiazol-6,11-dione |
| C56 | 4-(4-chloro-benzyl thio)anthra[2,1-c][1,2,5]thiadiazol-6,11-dione |
| C57 | 4-(4-tert-butyl benzyl thio)anthra[2,1-c][1,2,5]thiadiazol-6,11-dione |
| C58 | 4-(pyridin-2-yl-thio)anthra[2,1-c][1,2,5]thia-diazole-6,11-dione |

TABLE 1-continued

Thiadiazole fusion anthraquinone derivatives C1~C65

| NO. | IUPAC Name | R¹ structure |
|---|---|---|
| C59 | 4-(p-tolyloxy)anthra[2,1-c][1,2,5]thiadiazol-6,11-dione | 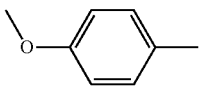 |
| C60 | 4-(4-chloro-phenylamino)anthra[2,1-c][1,2,5]thiadiazol-6,11-dione | 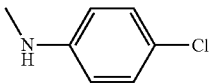 |
| C61 | 4-(o-tolylamino)anthra[2,1-c][1,2,5]thiadiazol-6,11-dione | 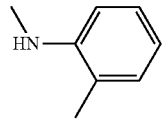 |
| C62 | 4-(m-tolylamino)anthra[2,1-c][1,2,5]thiadiazol-6,11-dione | 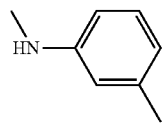 |
| C63 | 4-(3-chloro-phenylamino)anthra[2,1-c][1,2,5]thiadiazol-6,11-dione | 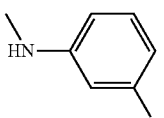 |
| C64 | 4-(p-tolylamino)anthra[2,1-c][1,2,5]thiadiazol-6,11-dione | 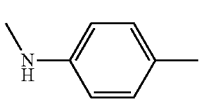 |
| C65 | 4-(4-chloro-2-fluoro-phenyl amino)anthra[2,1-c][1,2,5]thiadiazol-6,11-dione | 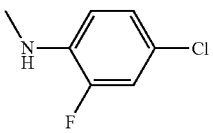 |

In addition, please refer to the first diagram, the first pictured preparation of the compound of C1~C65 flowchart. As illustrated, the present invention further provides a method for preparation of above mentioned heterocyclic fused anthraquinone derivatives as described below. First, 1.19 g (5 mmole) compound 1,2-diamino-anthraquinone was dissolved in 30 mL tetrahydrofuran (THF), and 0.15 g (20 mmol) thionyl chlorine was added dropwisely, and then 3 ml of triethylamine was added as catalysis, the reaction was stirred at room temperature for 24 hours. The reacted mixture was poured into ice water (200 mL), and precipitate was collected by filtration, and the precipitate with hot liquor precision re-crystallized, and was obtained as a yellow compound C1, yield is 74%.

Next, 5 mL concentrated hydrochloric acid and 0.05 g (2 mmole) compound C1 was added in 20 mL of glacial acetic acid heated under reflux for 45 minutes under 90° C., after that, added 1.50 g (12 mmole) of potassium chlorate (KClO₃) into the boiling mixture and the mixture was heated under reflux for 4 hours. The complete reacted mixture was placed into an ice water bath, and added a small amount of potassium hydroxide (KOH) to neutralize the acidity, and then precipitate the crude product. The precipitate was collected by filtration and recrystallization by acetic acid and obtained a yellow-orange compound C2, 72% yield.

Subsequently, anhydrous tetrahydrofuran and N,N-diisopropyl ethylamine mixed solution or ethylene glycol (depends on the needed reaction of C2 compound) and C2 was formed a mixed solution, and then added one of aminoalkyl, alkylthioalkyl group, halogen group, piperazinyl group, sulfonic acid group, morpholino group or metal salt substituent group containing to the mixed solution. Finally, depending on the reaction and the compound involved in the reaction, further heated to reflux in an ice bath, and concentrated, rinsed, precipitated and filtered to obtain the compound C3~C18.

Moreover, when the substituents added in the compound having the following formula, for example: p-chloroaniline, p-methyl phenol, benzene thiol type compounds, the final products are C19~C65 compounds:

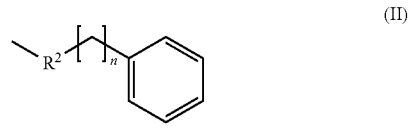

(II)

wherein, R² represents amino, oxy or thio group, and H of benzene in formula (II) can be substituted by halogen, alkoxy group, nitro group, methylthio group or sulfhydryl.

The present invention further provides the preparation method of compounds C3, 4, 5, 10, 15~21, 58~61 as follows. However, the present invention is not trying to limit the dosage, the ratio or the reaction time, any simple changing of the reaction parameters in order to achieve the same purpose also belong to the scope of the present invention.

EXAMPLE

Example 1

Sodium 6,11-dioxo-6,11-dihydroanthra[2,1-c][1,2,5]thiadiazole-4-sulfonate (Compound C3)

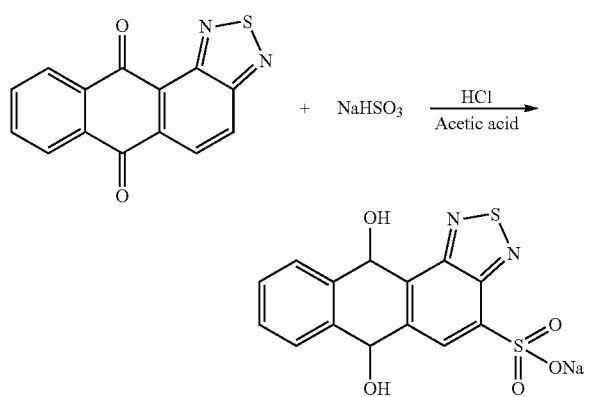

First, 4.58 g (40 mmole) sodium bisulfite (NaHSO₃) was dissolved in water to form a homogeneous solution of 4.5 N. Next, 2.66 g (10 mmole) compound C1 was added in 30 ml of water, 0.5 ml pyridine (pyridine) and 9 ml alkylene sodium bisulfate solution and boiled for 3 hours. Then added 4 g (68.96 mmole) of sodium chloride, cooled down, the sallow sodium salt precipitate was filtered. Sequentially washed with 5% sodium chloride solution, ethanol and diethyl ether to obtain an intermediate of 3.29 g bis hydroxyl (OH), yield 88%.

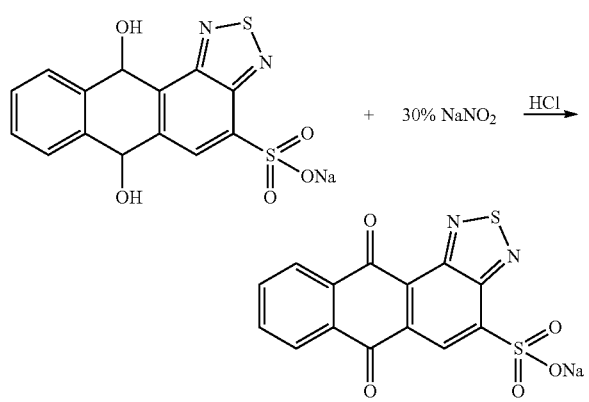

Next, 0.5 ml of concentrated hydrochloric acid and 0.4 ml of 30% sodium nitrite are mixed to form a homogeneous acid solution. The intermediate 0.37 g (0.001 mole) was suspended in 17 ml aqueous solution and the above-mentioned acid solution was added, and boiled for 3 minutes. Then added 30 ml of saturated NaCl solution, cooled down, crystallized the sodium salt and washed with 5% sodium chloride solution, water, ethanol, respectively, to obtain 0.31 g of compound C3, 77% yield.

melting point 293-295 t (dec.)

Mol. Wt. 367.95 ($C_{14}H_5NaN_2O_5S_2$)

¹H-NMR (300 MHz, DMSO-$d_6$) δ (ppm) 7.93-7.97 (2H, m, Ar—H), 8.20-8.24 (2H, m, Ar—H), 8.72 (1H, s, Ar—$H_5$), 9.09 (1H, s, –$SO_3OH$)

Example 2

Potassium 6,11-dioxo-6,11-dihydroanthra[2,1-c][1,2,5]thiadiazol-4-olate (Compound C4)

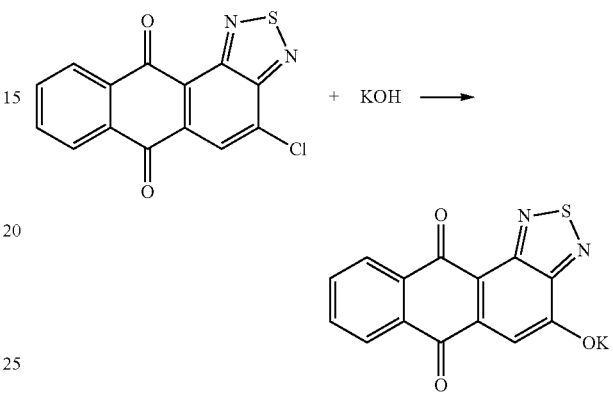

First, 0.12 g (2 mmole) of potassium hydroxide was dissolved in 4 ml of distilled water to form a homogeneous solution of 0.5 N. 0.3 g (1 mmole) compound C2 is stirred with 4 ml of potassium hydroxide for 30 minutes at room temperature to completely dissolved. The blue solution was set in a refrigerating compartment, overnight, to obtain compound C4, yield 83%.

Mol. Wt. 367.95 ($C_{14}H_5KN_2O_3S_2$)

¹H-NMR (300 MHz, DMSO-$d_6$) δ (ppm): 7.54 (1H, s, Ar—$H_5$), 7.76-7.80 (2H, m, Ar—H), 8.10-8.15 (2H, m, Ar—H), 10.59 (1H, s, Ar—OH)

Example 3

4-(diethylamino)anthra[2,1-c][1,2,5]thiadiazol-6,11-dione (Compound C5)

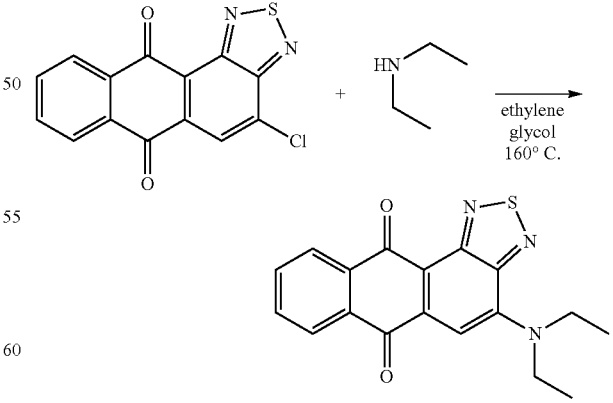

0.3 g (1 mmole) of compound C2 was dissolved in the glycol solution was stirred evenly inserted of diethylamine 0.09 g (1 mmole), the mixture was heated to 160° C., and refluxed for 0.5 hours. The reaction mixture was concentrated under reduced pressure and the aqueous solution was extracted with dichloromethane, dried over magnesium sulfate, after the crude product was concentrated under reduced pressure, recrystallization from ethanol, collected by filtration, to obtain purple compound C5, 80% yield.

melting point: 204-205° C.; Mol. Wt.: 337.40; Rf: 0.63 (ethyl acetate:n-hexane=2:3); HRMS (EI) m/z calcd [M]$^+$, 337.0885 ($C_{18}H_{15}N_3O_2S^+$); found, 337.0888.

$^1$H NMR (300 MHz, CDCl$_3$): δ ppm 1.43 (6H, t, J=7.2 Hz, —CH$_3$), 4.05 (4H, q, J=6.9 Hz, —NCH$_2$), 7.33 (1H, s, Ar—H$_5$), 7.70 (1H, td, J=7.5 Hz, J=1.2 Hz, Ar—H$_8$), 7.79 (1H, td, J=7.8 Hz, J=1.5 Hz, Ar—H$_9$), 8.21 (1H, dd, J=7.5 Hz, J=1.2 Hz, Ar—H$_{10}$), 8.35-8.38 (1H, m, Ar—H$_7$)

$^{13}$C NMR (75 MHz, CDCl$_3$): δ ppm 13.15, 47.40, 102.08, 112.84, 126.71, 127.27, 132.72, 132.81, 134.59, 135.12, 138.60, 145.78, 151.20, 155.44, 179.69, 185.22

Example 4

4-(morpholino)anthra[2,1-c][1,2,5]thiadiazol-6,11-dione (Compound C10)

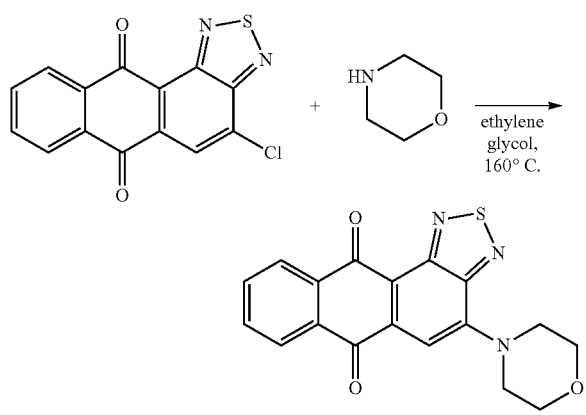

First, 0.3 g (1 mmole) compound C2 was dissolved in the ethylene glycol solution was stirred for uniform insertion of 0.09 g (1 mmole) morpholine, the mixture was heated to 160° C., and refluxed for 0.5 hours. The reaction mixture was concentrated under reduced pressure and the aqueous solution extracted with dichloromethane (dichloromethane/H$_2$O), after dehydration over magnesium sulfate (MgSO$_4$), the crude product was concentrated under reduced pressure, and ethanol recrystallization, collected by filtration to obtain dark brown compound C10, 70% yield.

melting point: 259-260° C.; Mol. Wt.: 351.38 ($C_{18}H_{13}N_3O_3S$); Rf: 0.84 (ethyl acetate:n-hexane=2:3); EIHR-MS m/z calcd. for $C_{18}H_{13}N_3O_3S^+[M]^+$=351.0678, Found: 351.0682

$^1$H-NMR (300 MHz, CDCl$_3$) δ (ppm): 3.98-4.01 (2H, m, —NCH$_2$—), 4.05-4.08 (2H, m, —OCH$_2$—), 7.55 (1H, s, Ar—H$_5$), 7.76 (1H, dd, J=7.5 Hz, J=1.5 Hz, Ar—H$_9$), 7.81 (1H, dd, J=7.5 Hz, J=1.5 Hz, Ar—H$_8$), 8.24 (1H, dd, J=7.5 Hz, J=1.2 Hz, Ar—H$_{10}$), 8.36 (1H, dd, J=7.5 Hz, J=1.2 Hz, Ar—H$_7$)

$^{13}$C-NMR (75 MHz, CDCl$_3$) δ (ppm): 49.88, 66.89, 105.32, 116.32, 126.97, 127.43, 132.68, 133.33, 134.42, 134.78, 138.12, 147.54, 150.84, 154.60, 180.50, 184.67

Example 5

4-(thiomorpholino)anthra[2,1-c][1,2,5]thiadiazol-6,11-dione (Compound C15)

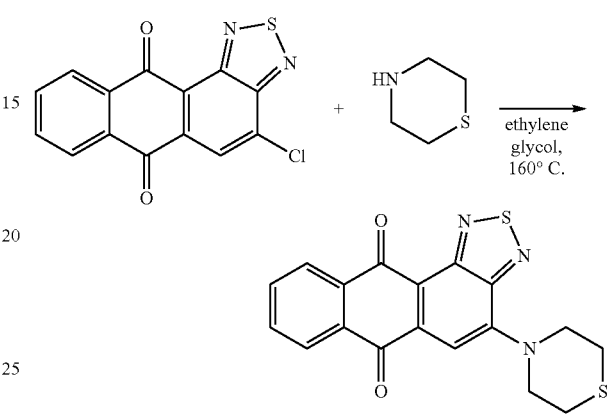

First, 0.3 g (1 mmole) compound C2 was dissolved in the above-mentioned ethylene glycol solution was stirred uniformly, and added 0.10 g (1 mmole) thiomorpholine, and the mixture was heated to 160° C. and refluxed for 0.5 hours. The reaction mixture was concentrated under reduced pressure and the aqueous solution was extracted with dichloromethane, dried over magnesium sulfate, after the crude product was concentrated under reduced pressure, recrystallization from ethanol, collected by filtration, to obtain a pale brown compound C15, 62% yield.

melting point: 219-220° C.; Mol. Wt.: 367.44 ($C_{18}H_{13}N_3O_2S_2$); Rf: 0.60 (ethyl acetate:n-hexane=2:3); EIHR-MS m/z calcd. for $C_{18}H_{13}N_3O_2S_2^+[M]^+$=367.0449, Found: 367.0444

$^1$H-NMR (300 MHz, CDCl$_3$) δ (ppm): 1.84 (4H, t, J=4.5 Hz, —SCH$_2$), 4.08 (4H, t, J=5.4 Hz, —NCH$_2$—), 7.51 (1H, s, Ar—H$_5$), 7.69 (1H, t, J=7.5 Hz, Ar—H$_8$), 7.76 (1H, t, J=7.5 Hz, Ar—H$_9$), 8.23 (1H, dd, J=7.5 Hz, J=1.5 Hz, Ar—H$_{10}$), 8.35-8.38 (1H, m, Ar—H$_7$)

$^{13}$C NMR (75 MHz, CDCl$_3$): δ ppm 27.65, 53.09, 105.68, 115.68, 126.79, 127.43, 132.54, 134.51, 134.66, 138.42, 147.10, 150.45, 154.59, 182.31, 184.93.

Example 6

4-(ethylthio)anthra[2,1-c][1,2,5]thiadiazol-6,11-dione (Compound C16)

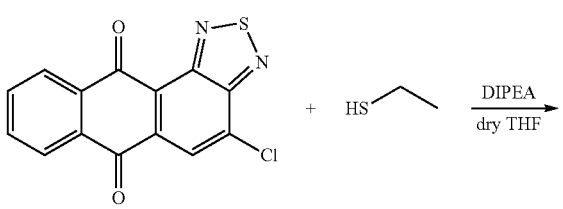

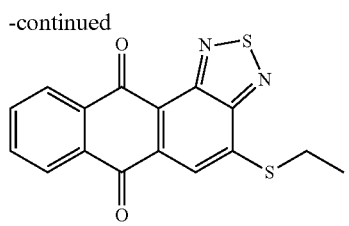

0.3 g (1 mmole) of compound C2 was dissolved in the anhydrous tetrahydrofuran with N,N-di-isopropylethylamine mixed solution was stirred uniformly, add 0.10 g 1 mmole of ethanethiol, and the mixture was heated to 65° C. and refluxed for 2 to 4 hours. Reaction mixture was concentrated under reduced pressure, after the magnesium sulfate aqueous solution was extracted with dichloromethane, the crude product was concentrated under reduced pressure, and ethanol recrystallization, collected by filtration, to obtain a compound of the dark brown C16 (yield 88%).

MP: 188-189° C. (EtOH); Rf: 0.78 (ethyl acetate:n-hexane=2:3); Mol. Wt. 326.39

$^1$H NMR (300 MHz, CDCl$_3$): δ ppm 1.57 (3H, t, J=7.5 Hz, —CH$_3$), 3.35 (2H, q, J=7.5 Hz, —SCH$_2$), 7.78-7.90 (2H, m, Ar—H$_{8,9}$), 8.14 (1H, s, Ar—H$_5$), 8.27 (1H, d, J=7.2 Hz, Ar—H$_{10}$), 8.35 (1H, d, J=6.9 Hz, Ar—H$_7$)

HRMS (EI) m/z: calcd [M]$^+$, 326.0184 (C$_{20}$H$_{10}$N$_2$O$_2$S$_3$$^+$); found, 326.0184.

Example 7

4-(n-propylthio)anthra[2,1-c][1,2,5]thiadiazol-6,11-dione (Compound C17)

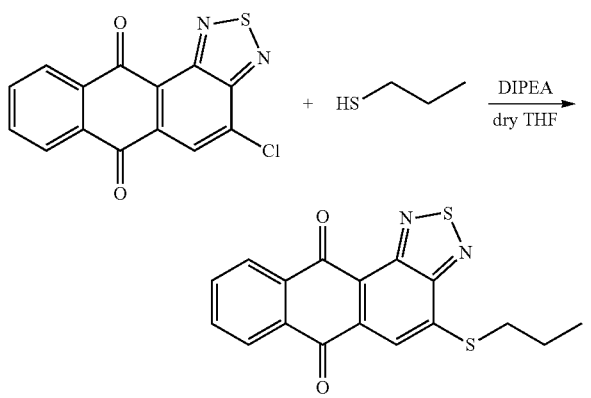

0.3 g (1 mmole) the compound C2 dissolved in the anhydrous tetrahydrofuran with N, N-di-isopropyl-ethylamine of the mixed solution was stirred uniformly, adding of 0.10 g 1 mmole the propane-1-thiol, the mixture was heated to 65° C. and refluxed for 2 to 4 hours. The reaction mixture was concentrated under reduced pressure, after the magnesium sulfate aqueous solution was extracted with dichloromethane, the crude product was concentrated under reduced pressure, and ethanol recrystallization was collected by filtration, to obtain a compound of the dark brown C17 (yield 85%).

(Rf): 0.80 (ethyl acetate:n-hexane=2:3); (Mol. Wt.): 340.42

$^1$H NMR (300 MHz, CDCl$_3$): δ ppm 1.20 (3H, t, J=7.2 Hz, —CH$_3$), 1.94 (2H, sext, J=7.2 Hz, —CH$_2$—), 3.29 (2H, t, J=7.2 Hz, —SCH$_2$), 7.80-7.88 (2H, m, Ar—H$_{8,9}$), 8.14 (1H, s, Ar—H$_5$), 8.28 (1H, dd, J=7.2 Hz, J=1.2 Hz, Ar—H$_{10}$), 8.36 (1H, dd, J=7.2 Hz, J=1.2 Hz, Ar—H$_7$).

$^{13}$C NMR (75 MHz, CDCl$_3$): δ ppm 13.63, 21.78, 33.56, 118.47, 121.02, 127.16, 127.49, 127.60, 132.37, 134.01, 134.98, 135.64, 143.04, 151.22, 155.94, 181.73, 183.96.

HRMS (EI) m/z: calcd [M]$^+$, 340.0340 (C$_{20}$H$_{10}$N$_2$O$_2$S$_3$$^+$); found, 340.0338.

Example 8

4-(isopropylthio)anthra[2,1-c][1,2,5]thiadiazol-6,11-dione (Compound C18)

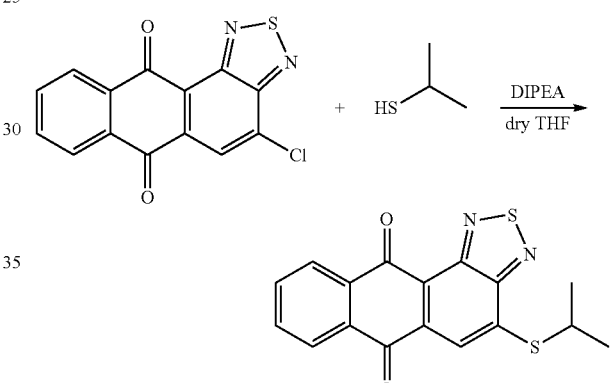

0.3 g (1 mmole) of compound C2 was dissolved in the anhydrous tetrahydrofuran with N,N-di-isopropylethylamine mixed solution was stirred uniformly, adding of 0.10 g 1 mmole the propane-2-thiol, the mixture was heated to 65° C., refluxed for 2 to 4 hours. The reaction mixture was concentrated under reduced pressure and the aqueous solution was extracted with dichloromethane, dried over magnesium sulfate, after the crude product was concentrated under reduced pressure, recrystallization from ethanol, collected by filtration to obtain yellow compound C18 (yield 88%). Rf: 0.88 (ethyl acetate:n-hexane=2:3)

Mol. Wt.: 340.42; MP: 193-194° C. (EtOH). HRMS (EI) m/z: calcd [M]$^+$, 340.0340 (C$_{20}$H$_{10}$N$_2$O$_2$S$_3$$^+$); found, 340.0345.

$^1$H NMR (300 MHz, CDCl$_3$): δ ppm 1.57 (6H, d, J=6.6 Hz, —CH$_3$), 4.05 (1H, t, J=6.9 Hz, —SCH—), 7.81-7.89 (2H, m, Ar—H$_{8,9}$), 8.23 (1H, s, Ar—H$_5$), 8.27-8.30 (1H, m, Ar—H$_{10}$), 8.36-8.39 (1H, m, Ar—H$_7$).

$^{13}$C NMR (75 MHz, CDCl$_3$): δ ppm 22.81, 36.08, 119.67, 121.17, 127.17, 127.51, 127.82, 132.40, 134.03, 134.98, 135.64, 142.33, 151.36, 156.24, 181.77, 183.95.

Example 9

4-(phenylthio)anthra[2,1-c][1,2,5]thiadiazol-6,11-dione (Compound C19)

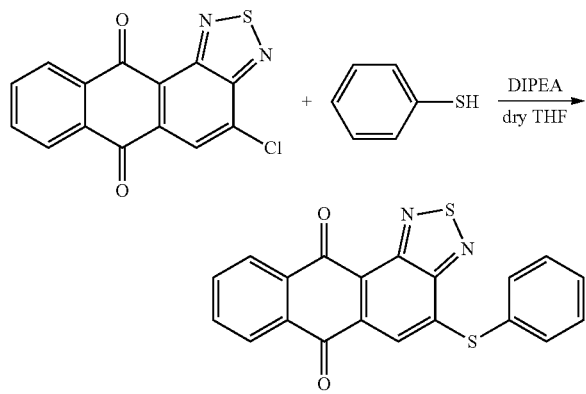

Take 0.3 g (1 mmole) the compound C2 dissolved in the anhydrous tetrahydrofuran with N,N-di-isopropyl ethylamine mixed solution was stirred for uniform insertion of 0.11 g (1 mmole) benzenethiol, and the mixture was heated to 65° C. and reflux reacted for 2 to 4 hours. The complete reaction mixture was concentrated under reduced pressure and the aqueous solution was extracted with dichloromethane, dried over magnesium sulfate, after the crude product was concentrated under reduced pressure, recrystallization from ethanol, collected by filtration, to obtain orange compound C19, 76% yield.

melting point: 224~1214° C. (EtOH); Mw: 374.44; retention factor, Rf: 0.57 (ethyl acetate: n-hexane=2:3)

EIHR-MS m/z calcd. for $C_{20}H_{10}N_2O_2S_2^+[M]^+=374.0184$, found: $[M]+=374.0184$ $^1$H-NMR (300 MHz, CDCl$_3$) δ (ppm): $^1$H NMR (300 MHz, CDCl$_3$): 7.58-7.62 (3H, m, Ar'—H$_{2,4,6}$), 7.71-7.74 (2H, m, Ar'—H$_{3,5}$), 7.76-7.86 (3H, m, Ar—H$_{5,8,9}$), 8.16 (1H, dd, J=7.8 Hz, J=1.5 Hz, Ar—H$_{10}$), 8.35 (1H, dd, J=7.8 Hz, J=1.5 Hz, Ar—H$_7$)

$^{13}$C NMR (75 MHz, CDCl$_3$): δ ppm 119.96, 121.40, 127.08, 127.47, 128.32, 130.67, 130.87, 132.30, 133.97, 134.06, 134.88, 135.93, 143.62, 151.32, 155.18, 180.51, 183.41.

Example 10

4-(2,5-dimethyl-phenyl-thio)anthra[2,1-c][1,2,5]thiadiazol-6,11-dione (Compound C20)

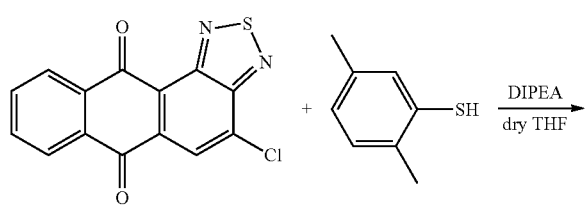

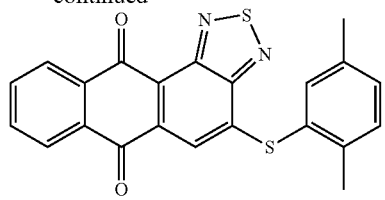

Taken 0.3 g (1 mmole) compound C2 was dissolved in the above anhydrous tetrahydrofuran and N,N-diisopropyl ethylamine to the mixed solution was stirred uniformly, insertion of 0.14 g (1 mmole) 2,5-dimethylphenoxy thiophenol, mixed The solution was heated to 65° C., and refluxed for 2 to 4 hours. The complete reaction mixture was concentrated under reduced pressure and the aqueous solution was extracted with dichloromethane, dried over magnesium sulfate, after the crude product was concentrated under reduced pressure, recrystallization from ethanol, collected by filtration, to obtain a dark brown compound C20, 47% yield.

Melting Point: 243-244° C.; Mw: 402.49; Rf: 0.74 (ethyl acetate:n-hexane=2:3); EIHR-MS m/z calcd; $C_{22}H_{14}N_2O_2S_2^+[M]^+=402.0497$, found $[M]^+=402.0506$.

$^1$H-NMR (300 MHz, CDCl$_3$) δ (ppm): 2.40 (6H, s, —CH$_3$), 7.33 (1H, d, J=7.8 Hz, Ar'—H$_4$), 7.39 (1H, d, J=7.5 Hz, Ar'—H$_3$), 7.51-7.53 (2H, m, Ar—H$_5$, Ar'—H$_6$), 7.76 (1H, t, J=7.5 Hz, Ar—H$_8$), 7.83 (1H, t, J=7.8 Hz, Ar—H$_9$), 8.15 (1H, d, J=7.5 Hz, Ar—H$_{10}$), 8.34 (1H, d, J=7.5 Hz, Ar—H$_7$)

$^{13}$C NMR (75 MHz, CDCl$_3$): δ ppm 20.11, 20.85, 119.14, 121.23, 125.36, 126.99, 127.42, 127.75, 131.75, 132.45, 134.01, 134.05, 134.92, 135.12, 137.52, 137.99, 140.58, 143.96, 149.25, 156.50, 180.41, 183.51.

Example 11

4-(benzyl-thio)anthra[2,1-c][1,2,5]thiadiazol-6,11-dione (Compound C21)

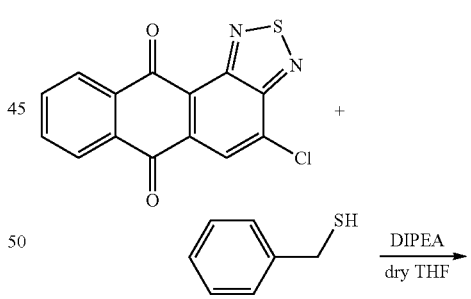

0.3 g (1 mmole) compound C2 was dissolved in the above anhydrous tetrahydrofuran and N,N-diisopropyl ethylamine, a mixed solution was stirred for uniform insertion of 0.12 g (1 mmole) of phenyl methyl mercaptan, and the mixture was heated to 65° C., refluxed for 2 to 4 hours. The reaction mixture was concentrated under reduced pressure to obtain a pale brown compound C21 of the aqueous solution was extracted with dichloromethane, dried over magnesium sulfate, after the crude product was concentrated under reduced pressure, recrystallization from ethanol, collected by filtration, and (88% yield).

Rf: 0.72 (ethyl acetate:n-hexane=2:3); Mp: 243-244° C.; Mw: 388.46

EIHR-MS m/z calcd. for $C_{21}H_{12}N_2O_2S_2{}^+[M]^+=388.0340$, found: $[M]^+=388.0340$ $^1$H-NMR (300 MHz, CDCl$_3$) δ (ppm): 3.97 (2H, s, —CH$_2$—), 7.69 (1H, s, Ar—H$_5$), 7.31-6.65 (5H, m, Ar—H'$_{2,3,4,5,6}$), 7.70 (1H, td, J=7.5 Hz, J=1.2 Hz, Ar—H$_9$), 7.72 (1H, td, J=7.5 Hz, J=1.2 Hz, Ar—H$_8$), 8.20-8.23 (1H, m, Ar—H$_{10}$), 8.29-8.32 (1H, m, Ar—H$_7$)

$^{13}$C-NMR (75 MHz, CDCl$_3$) δ (ppm): 28.15, 125.76, 126.13, 127.40, 127.58, 128.16, 128.73, 129.32, 130.12, 131.23, 132.01, 132.43, 133.21, 133.45, 134.45, 135.88, 136.34, 151.32, 154.70, 183.02, 185.71

Example 12

4-(pyridin-2-yl-thio)anthra[2,1-c][1,2,5]thiadiazol-6,11-dione (Compound C58)

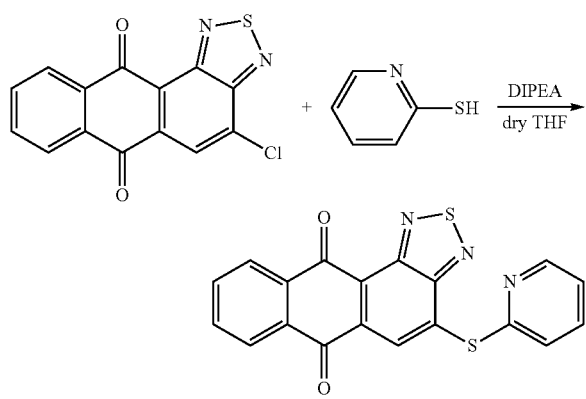

0.5 ml of N,N-diisopropylethylamine in 25 ml of anhydrous tetrahydrofuran were mixed to form a homogeneous solution, and set aside. Take 0.3 g (1 mmole) of compound C2 was dissolved in the above anhydrous tetrahydrofuran and N,N-diisopropyl ethylamine mixed solution was stirred uniformly, and insertion of 0.11 g (1 mmole) of 2-mercaptopyridine, and the mixture was heated to 65° C., refluxed for 2 to 4 hours. Complete reaction the mixture was concentrated under reduced pressure, after the magnesium sulfate aqueous solution was extracted with dichloromethane, the crude product was concentrated under reduced pressure, and ethanol recrystallization, collected by filtration, to obtain the compound of the orange-red C58 (yield 37%).

melting point: 225-226° C.; Rf: 0.72 (ethyl acetate:n-hexane=2:3); EIHR-MS m/z calcd. for $C_{19}H_9N_3O_2S_2{}^+$ $[M]^+=375.0136$, found: 375.0130

$^1$H-NMR (300 MHz, CDCl$_3$) δ (ppm): 7.31-7.35 (1H, m, Ar'—H$_4$), 7.62 (1H, dt, J=7.8 Hz, J=1.2 Hz, Ar'—H$_6$), 7.75-7.88 (1H, m, Ar—H$_{8,9}$, Ar'—H$_5$), 8.22-8.25 (1H, m, Ar—H$_{10}$), 8.35-8.338 (1H, m, Ar—H$_7$), 8.45 (1H, s, Ar—H$_5$), 8.62 (1H, dd, J=4.8 Hz, J=0.9 Hz, Ar—H$_3$).

Example 13

4-(p-tolyloxy)anthra[2,1-c][1,2,5]thiadiazol-6,11-dione (Compound C59)

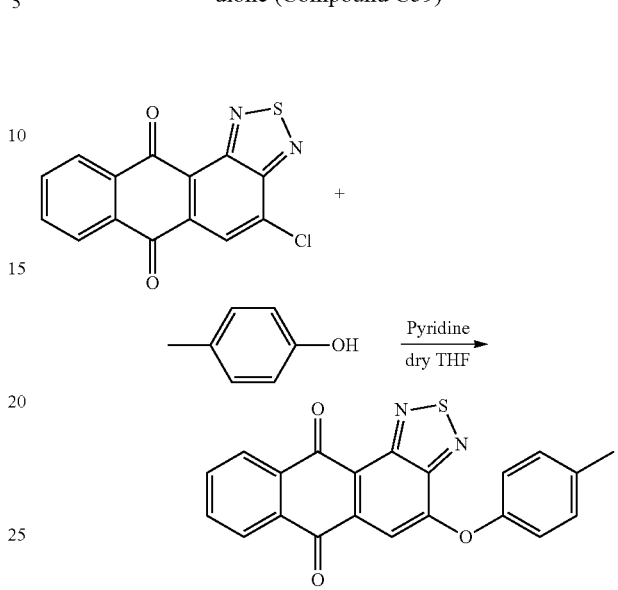

25 ml anhydrous tetrahydrofuran mixed to form a uniform solution of 0.5 ml of pyridine, and set aside. Take 0.3 g (1 mmole) of compound C2 dissolved in the anhydrous tetrahydrofuran with pyridine and a mixed solution was stirred uniformly, insertion of 0.11 g (1 mmole) p-methyl phenol, and the mixture was heated to 65° C. and refluxed for 2 to 4 hours. The complete reaction mixture was concentrated under reduced pressure, the aqueous solution was extracted with methylene chloride, magnesium sulfate, the crude product was concentrated under reduced pressure, recrystallization from ethanol, collected by filtration, obtain red purple compound C59, 35% yield.

melting point: 244-245° C.; Mol. Wt.: 372.06 ($C_{21}H_{12}N_2O_3S$); Rf: 0.57 (ethyl acetate: n-hexane=2:3)

Example 14

4-(4-chloro-phenylamino)anthra[2,1-c][1,2,5]thiadiazol-6,11-dione (Compound C60)

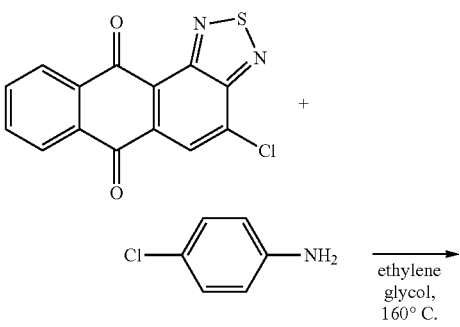

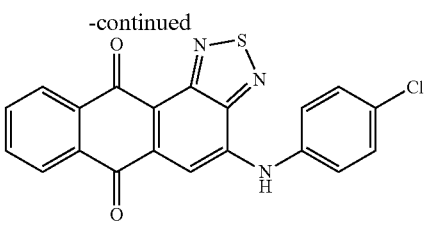

0.57 g (2 mmole) compounds C2 dissolved in ethylene glycol solution Stir, add 0.77 g (6 mmole) right-chloro-aniline, and the mixture was heated to 160° C., and refluxed for 0.5 hours. The set was cooled to 80° C. quickly in hot water to precipitate after filtration, the crude product after drying, to recrystallization from ethanol, the purple compound C60, 55% yield.

melting point: 306-307° C.; Mol. Wt.: 391.83 ($C_{20}H_{10}ClN_3O_2S$); Rf: 0.37 (ethyl acetate:n-hexane=2:3)

$^1$H-NMR (300 MHz, CDCl$_3$) δ (ppm): 7.42 (2H, d, J=7.8 Hz, Ar'—H$_{3,5}$), 7.48 (2H, d, J=7.8 Hz, Ar'—H$_{2,6}$), 7.72-7.78 (1H, m, Ar—H$_9$), 7.80-7.85 (1H, m, Ar—H$_8$), 7.85 (1H, s, Ar—H$_5$), 8.22 (1H, dd, J=7.5 Hz, J=1.5 Hz, Ar—H$_{10}$), 8.35-8.38 (1H, m, Ar—H$_7$).

HRMS (EI) m/z: calcd [M]$^+$, 391.0182 ($C_{20}H_{10}ClN_3O_2S^+$); found, 391.0183.

Example 15

4-(-o-tolylamino)anthra[2,1-c][1,2,5]thiadiazol-6,11-dione (Compound C61)

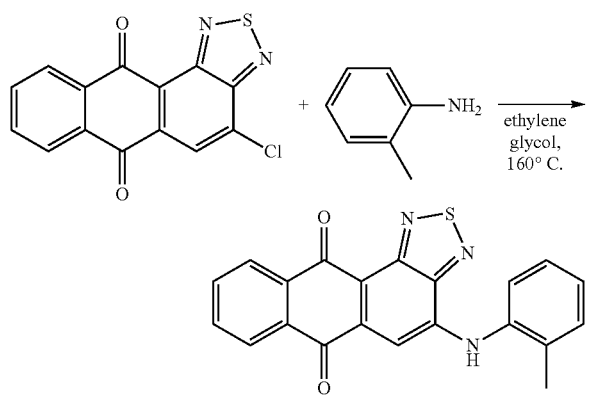

0.57 g (2 mmole) was dissolved in ethylene glycol solution, compound C2 stir, add 0.84 ml (6 mmole) 2-methyl aniline, and the mixture was heated to 160° C., and refluxed for 0.5 hours. The set was cooled to 80° C. quickly in hot water to precipitate after filtration, the crude product after drying, to recrystallization from ethanol, to obtain a purple compound C61, 28% yield.

melting point: 177-178° C.; Mol. Wt.: 371.41 ($C_{21}H_{13}N_3O_2S$); Rf: 0.49 (ethyl acetate:n-hexane=2:3)

$^1$H NMR (300 MHz, CDCl$_3$): δ ppm 2.37 (3H, s, —CH$_3$), 7.29 (1H, d, J=7.2 Hz, Ar'—H$_6$), 7.34-7.40 (2H, m, Ar'—H$_{4,5}$), 7.49 (1H, s, Ar—H$_5$), 7.52 (1H, d, J=7.2 Hz, Ar'—H$_3$), 7.72 (1H, td, J=7.5 Hz, J=1.5 Hz, Ar—H$_9$), 7.80 (1H, td, J=7.5 Hz, J=1.5 Hz, Ar—H$_8$), 8.19 (1H, dd, J=7.8 Hz, J=1.2 Hz, Ar—H$_{10}$), 8.36 (1H, d, J=7.8 Hz, Ar—H$_7$).

$^{13}$C NMR (75 MHz, CDCl$_3$): δ ppm 17.86, 100.55, 115.84, 125.01, 126.82, 126.93, 127.30, 127.71, 131.95, 132.71, 133.25, 133.39, 134.35, 134.67, 136.57, 139.74, 142.68, 150.15, 153.25, 180.52, 184.54.

Further, the present invention also provides a compound of C29, C53, C56, C57 with the relevant physical data to further prove that the method of preparation in the present invention provides the heterocyclic fused anthraquinone derivatives. First, compound C29 prepared by the method of the present invention was 62% Yield. Melting point: 119-120° C., Mol. Wt.: 402.49 ($C_{22}H_{14}N_2O_2S_2$), other data shows that: Rf: 0.84 (ethyl acetate:n-hexane=2:3); EIHR-MSm/z calcd. For $C_{22}H_{14}N_2O_2S_2^+$[M]$^+$=402.0497, found: 402.0491; $^1$H-NMR (300 MHz, CDCl$_3$) δ (ppm): 3.11 (2H, t, J=7.5 Hz, —CH$_2$—), 3.58 (2H, t, J=7.5 Hz, —SCH$_2$—), 7.23-7.37 (5H, m, Ar'—H$_{2,3,4,5,6}$), 7.81-7.88 (2H, m, Ar—H$_{8,9}$), 8.22 (1H, s, Ar—H$_5$), 8.25 (1H, dd, J=7.5 Hz, J=1.5 Hz, Ar—H$_{10}$), 8.37 (1H, dd, J=7.5 Hz, J=1.5 Hz, Ar—H$_7$).

Next, the compound C53 Yield is 81%, melting point: 254-255° C. Mol. Wt. Is 422.91 ($C_{21}H_{11}ClN_2O_2S_2$), other data as follows: Rf: 0.92 (ethyl acetate:n-hexane=2:3); EIHR-MS m/z calcd. for $C_{23}H_{16}N_2O_2S_2^+$[M]$^+$=421.9950, found: 421.9954; $^1$H-NMR (300 MHz, CDCl$_3$) δ (ppm): 4.67 (2H, s, —CH$_2$—), 7.52-7.28 (2H, dd, J=7.2 Hz, J=1.8 Hz, Ar'—H$_{3,6}$), 7.44-7.47 (1H, m, Ar'—H$_5$), 7.56-7.59 (1H, m, Ar'—H$_4$), 7.80-7.86 (2H, m, Ar—H$_{8,9}$), 8.26 (1H, dd, J=7.5 Hz, J=1.5 Hz, Ar—H$_{10}$), 8.27 (1H, s, Ar—H$_5$), 8.35 (1H, dd, J=7.5 Hz, J=1.5 Hz, Ar—H$_7$).

Compound C56 Yield is 82%, melting point: 261-262° C. Mol. Wt. Is 422.91 ($C_{21}H_{11}ClN_2O_2S_2$), other data as follows: Rf: 0.86 (ethyl acetate:n-hexane=2:3); EIHR-MSm/z calcd. for $C_{22}H_{14}N_2O_2S_2^+$[M]$^+$=421.9950, found: 421.9942; $^1$H-NMR (300 MHz, CDCl$_3$) δ (ppm): 4.52 (2H, s, —CH$_2$—), 7.34 (2H, d, J=8.4 Hz, Ar'—H$_{2,6}$), 7.48 (2H, d, J=7.8 Hz, Ar'—H$_{3,5}$), 7.81-7.86 (2H, m, Ar—H$_{8,9}$), 8.24 (1H, s, Ar—H$_5$), 8.27 (1H, d, J=7.2 Hz, Ar—H$_{10}$), 8.36 (1H, d, J=7.2 Hz, Ar—H$_7$).

Compound C57 Yield is 62%, melting point: 256-257° C. Mol. Wt.: 444.57, other data as follows: Rf: 0.91 (ethyl acetate:n-hexane=2:3); HRMS (EI) m/z calcd [M]$^+$, 444.0966 ($C_{25}H_{20}N_2O_2S_2^+$), found, 444.0970; $^1$H NMR (300 MHz, CDCl$_3$): δ ppm 1.31 (9H, s, —CH$_3$), 4.26 (2H, s, —CH$_2$—), 7.39 (2H, d, J=8.4 Hz, Ar'—H$_{2,6}$), 7.35 (2H, d, J=8.4 Hz, Ar'—H$_{3,5}$), 7.83 (2H, td, J=7.5 Hz, J=1.8 Hz, Ar—H$_{8,9}$), 8.27-8.30 (2H, m, Ar—H$_{5,10}$), 8.36 (1H, d, J=7.2 Hz, Ar—H$_7$).

Further, the present invention can also provides a different approach to synthesize a series of compounds, which means Compound C2 formed by the C1 after chlorination and then to synthesize a series of compounds, but later, the present invention also provides C1 as a starting was to synthesize a series of derived compounds (C3-C65), and adding a metal to the entire one-step reaction as a catalyst, for example: copper acetate (I) and ferric chloride, because it is a step, so also relatively reduces the total reaction time, and the relative yield also increased a lot.

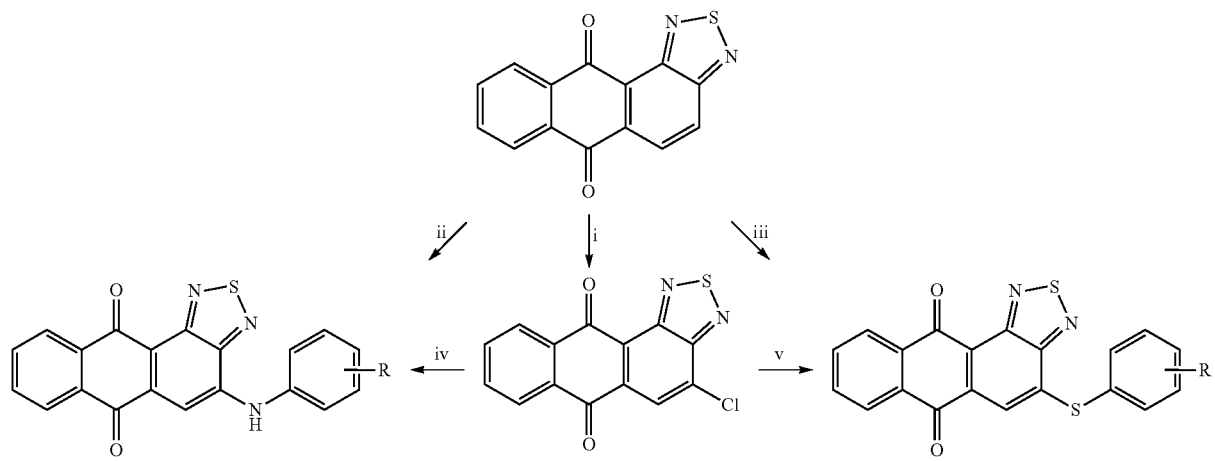

(i). KClO₃, Acetic acid, HCl, 90° C., 5 hr
(ii). Series aniline derivatives, copper acetate (I), DMF, 75° C., 2 hr
(iii). Series thiophenol derivatives, ferric chloride, DMF, 90° C., 3 hr~4 hr
(iv). Series aniline derivatives, ethylene glycol, 160° C., 30 mins
(v). Series thiophenol derivatives, DIPEA, dry THF, 65° C., 2 hr~4 hr Furthermore, the present invention further provides a pharmaceutical composition for treating cancer, which comprises a thiazole fused anthraquinone derivatives as formula I or the pharmaceutical acceptable salt and carrier thereof.

Preferably, the pharmaceutical acceptable salt is inorganic acid or organic acid or base physiological acceptable salt, the inorganic acid can be selected from the group consisting of HCl, HBr, $H_2SO_4$, sulfonic acid and $H_2PO_3$, wherein the organic salt can be selected from the group of citric acid, acetic acid, maleic acid, fumaric acid, gluconic acid, glycolic acid, methanesulfonic acid, succinic acid and galactose.

Preferably, the carrier is excipient agent, diluting agent, thickening agent, bulking agent, binder, disintegrating agent, lubricating agent, oil or non-oil based agent, surfactant, suspending agent, gelating agent, supporting agent, preservative agent, anti-oxidative agent, stabilizing agent, coloring agent or fragrance. Preferably, the excipient agent includes microcrystalline cellulose, polyvinylpyrrolidone, corn starch, modified starch, carboxymethyl stach sodium, polystyrenre, gelatinized starch, sugar, polyethylene glycol, polyvinyl alcohol, hypromellose, carboxymethyl cellulose, hydroxymethylcellulose or hydroxypropyl methylcellulose.

In addition, as mentioned before, the present invention provides a pharmaceutical composition for inhibiting a non-nucleoside telomerase. The pharmaceutical composition exists as a powder, a granule, a liquid, a colloid or a paste, and is accessible through the oral, transdermal absorption, injection or inhalation transmission.

In pharmacological test, we further use heterocyclic fusion anthraquinone derivatives of the present invention to test the pharmacological activity, so as to illustrate heterocyclic fusion anthraquinone derivatives of formula I-containing therapeutic pharmaceutical composition do have cancer efficacy and development. That means, the human tumor cell line cytotoxicity is assessed by analysis of cell survival via the in vitro experiments (SRB assay) and the American Cancer Institute (National. Cancer Institute, NCI) screening platform, which is showed as the Table II (PC-3 prostate cancer cell line, 50% of the proliferation of cancer cells suppressed sample concentration ($IC_{50}$)) and Table 3 (one-dose single concentration screening), respectively.

First, sulfonylurea rhodamine B-protein analysis (by the cytoplasm measured at the protein content of the sum of a representative sample of the total number of cells) can be used for the measurement of cell proliferation and survival. The negative protein of sulfonic acid in sulfonylurea rhodamine (SRB) dye is used in acidic environment to bind with alkaline amino acid of cytoplasm to colorize. And the SRB is extracted by weak alkaline solution in cell and measure the absorbance, and enzyme immunoassay analyzer (ELISA readerconverter) was used to measure the absorbance based on the concentration of cells—absorbance calibration curve measuring absorbance at a wavelength of 490 nm to obtain the real cell number charts, and statistical calculated the sample concentration of 50% of cancer cell proliferation inhibition. Basically, the cell viability analysis method is as follows: establishing a standard curve, and adding the experimental medium (DMEM) into a known concentration of cells by 2-fold serial dilution of the liquid (104 to 105), so that disk cell fluid volume of each aperture of 96-well plates is 100 µL, and incubating for 24 hours, removing the old medium. Adding 100 µL, 10% ice trichloroacetic acid (trichloroacetic acid, TCA), and incubating for 30 minutes at 4° C. within each aperture disk, then washing with water 5 times to remove TCA, the medium and dead cells. After completely dry (the orifice disk may be placed in a 37° C. oven drying) adding 50 µL, 4% (w/v) SRB dye at each aperture disk, standing for 15 minutes (to be dark), washing the aperture disk within the cells evenly with 1% acetic acid to remove non-binding SRB until the excess SRB is not exited in plate. After completely dry, re-adding 100 µL of 10 mM tris (hydroxymethyl)aminomethane buffer (Tris buffer) (pH 10.5) into each aperture disk to dissolve bonded dye of cell. Shaking for 15 to 30 minutes so that the agent was resuspended in the shaker, and measuring the absorption value of the wavelength at 490 nm by enzyme immune analyzer, to establish cell concentration—absorbance calibration curve. The data read by enzyme immunoassay analyzer fluorescent absorbance value for each sample was compared with pre-established cell concentration-absorbance calibration curve control, and obtaining a sample cell concentration as Table II.

Next, the American Institute for Cancer Research (National Cancer Institute, NCI) screening platform assessed the human tumor cell lines, and the cytotoxic cell lines were classified as acute lymphoblastic leukemia cell line (CCRF-CEM), bone marrow leukemia cell line (HL-60, TB) precursor, acute lymphoblastic leukemia cell line (MOLT-4), the standard risk-type cell line (Standard risk, SR), the PRMI-8226 cell line, the K562cell line and other leukemia cancer cell lines (Leukemia).

The non-small cell lung cancer cell lines (Non-Small Cell Lung Cancer) includes EKVX, HOP-62HOP-92, NCI-H226, NCI-H23, NCI-H322M, NCI-H460, NCI-H522, A549/ATCC series. Rectal cancer cell lines (COLO 205), colon cancer cell lines (HCC-2998, HCT-116, HCT-15, KM12, SW-620), colorectal tumors (Colon Cancer) cell lines (HT29) series. The tumor cell lines of central nervous system (CNS CANCER) includes SF-268, SF-295, SF-539, SNB-19, SNB-75, the glial tumor cell line (U251). Melanoma cell lines include LOX IMVI, MALME-3M, M14, UACC-62, UACC-257, the skin melanoma cell lines SK-MEL-2, SK-MEL-28, SK-MEL-5 cell strain. Ovarian cancer (Ovarian Cancer) cell line includes IGROV1, OVCAR-3, OVCAR-4, OVCAR-5, OVCAR-8, SK-OV-3 and other cell lines. Renal cell carcinoma includes clear cell renal cell adenoma (786-O, CAKI-1) cell lines, renal tumor cell line (A489, ACHN, SN12C, TK-10, UO-31 RXF, 393) and other cell lines (Renal Cancer). Prostate tumor cell lines (Prostate Cancer) are DU145, PC-3. Breast tumor cell line (Breast Cancer) includes MCF7, HS 578-T, MDA-MB-231/ATCC, MDA-MB-468, NCI/ADR-RES, the breast duct tumor cell lines BT-549, T-47D, MDA, -MB-435 and so on. From the data of American Cancer Center point of view, after structural modification, a series of derivative compounds even have higher anticancer activity than the starting material such as compounds C1 and C2. These compounds have a better potential to become antitumor compounds.

In cell viability analysis, we found that the compound with two carbons linking in PC-3 prostate cancer cells has the best performance. For example, in compound C19 ($IC_{50}$>15 μM) (no carbon), compound C21 ($IC_{50}$>15 μM) (linked by one carbon), compound C29 ($IC_{50}$=19 μM) (linked by two carbons), compound C29 (linked by three carbon), compound 29 has best performance. To compare the compound C32 and the compound C33 ($IC_{50}$ is >15 μM and 5.48 μM), both in the place of ortho chlorine substituent presence or absence of these two compounds, the compound with linker has relative good performance. Compound C22 and compound C56 has the same regularity. Therefore, to discuss about the SAR (structure and activity relationship) and anti-cancer cytotoxic ability, the overall structure must have a link to be a binder as the connection between the branched chain extension links. In addition, in vitro cell viability analysis (SRB assay) data, we can conclude the exact value of the $IC_{50}$, $IC_{50}$ of some of the compounds, some compounds even reach the level of less than 1 μM.

TABLE II

| SRB assay: 50% inhibition of cancer cell proliferation of sample concentration ($IC_{50}$) of PC-3 prostate cancer cell line | | | |
|---|---|---|---|
| compound | $IC_{50}$ | compound | $IC_{50}$ |
| C1 | 2.5 | C2 | 13.5 |
| C3 | 13.3 | C4 | 18.5 |
| C19 | 28.6 | C10 | 3.75 |
| C20 | 7.44 | C15 | >15 |
| C21 | >15 | C16 | 5.39 |
| C22 | >15 | C17 | 3.69 |
| C23 | >15 | C18 | 1.15 |
| C24 | >15 | C50 | >15 |
| C25 | >15 | C51 | >15 |
| C26 | >15 | C50 | >15 |
| C27 | 5.76 | C51 | >15 |
| C28 | 6.7 | C52 | >15 |
| C29 | 19.0 | C53 | 5.84 |
| C30 | 11.0 | C54 | 7.5 |
| C31 | >15 | C55 | 6.74 |
| C32 | >15 | C56 | >15 |
| C33 | >15 | C57 | 7.47 |
| C34 | >15 | C59 | N.T. |
| C35 | >15 | C60 | 9.5 |
| C36 | >15 | C61 | 0.21 |
| C37 | 5.64 | C62 | 0.29 |
| C38 | 8.82 | C63 | 2.28 |
| C39 | 14.82 | C64 | 0.84 |
| C40 | 12.4 | C65 | >15 |
| C41 | >15 | C5 | 1.10 |
| C42 | >15 | C6 | 3.25 |
| C43 | >15 | C7 | >15 |
| C44 | >15 | C8 | 0.40 |
| C45 | 8.38 | C9 | 9.43 |
| C46 | >15 | C11 | 1.38 |
| C47 | >15 | C12 | 1.76 |
| C48 | >15 | C13 | 2.97 |
| C49 | >15 | C14 | 0.74 |

TABLE 3

| Cytotoxicity assessment of human tumor cell lines by American Institute for Cancer Screening platform | | | | | |
|---|---|---|---|---|---|
| Panel/Cell Line | Compounds | | | | |
| Growth Percent $^a$ (10 μM) NSC number | C1 NSC745884 | C2 NSC757963 | C19 NSC757964 | C21 NSC757965 | C22 NSC757966 |
| Leukemia | | | | | |
| CCRF-CEM | −30.81 | −41.78 | 15.74 | 0.65 | 79.34 |
| HL-60(TB) | −21.77 | 1.87 | 83.94 | 70.32 | 87.34 |
| K562 | 49.61 | 2.44 | 52.03 | 10.51 | 94.91 |
| MOLT-4 | −40.09 | −34.12 | 31.08 | −20.97 | 59.21 |
| RPMI-8226 | −27.97 | 27.81 | 78.21 | 43.23 | 90.15 |
| SR | 4.96 | −23.86 | 86.41 | 1.25 | 110.89 |

TABLE 3-continued

Cytotoxicity assessment of human tumor cell lines by American Institute for Cancer Screening platform

| Non-small cell lung cancer | | | | | |
|---|---|---|---|---|---|
| A549/ATCC | 104.19 | 103.21 | 105.68 | 101.64 | 103.88 |
| HOP-62 | 103.18 | 82.19 | 97.77 | 94.98 | 94.80 |
| HOP-92 | −100.00 | 75.8 | 110.22 | 83.65 | 101.98 |
| NCI-H226 | N.T. | −52.25 | 117.67 | −14.36 | 94.77 |
| NCI-H23 | 97.80 | 100.39 | 101.59 | 101.09 | 104.26 |
| NCI-H322M | 16.07 | 75.02 | 79.21 | 55.30 | 100.11 |
| NCI-H460 | 125.82 | 108.2 | 100.74 | 98.44 | 99.52 |
| NCI-H522 | 77.41 | 100.18 | 100.56 | 92.01 | 102.62 |
| NCI-H226 | N.T. | 89.53 | 94.91 | 78.90 | 93.41 |
| Colon cancer | | | | | |
| COLO 205 | 111.54 | 99.08 | 117.53 | 102.93 | 121.41 |
| HCC-2998 | −0.74 | 105.67 | 110.88 | 115.02 | 106.82 |
| HCT-116 | −50.00 | 48.15 | 90.08 | 53.06 | 98.25 |
| HCT-15 | 1.48 | 96.8 | 93.89 | 54.72 | 98.10 |
| HT29 | 116.95 | N.T. | N.T. | N.T. | N.T. |
| KM12 | 98.60 | 95.88 | 99.5 | 103.02 | 101.50 |
| CNS cancer [b] | | | | | |
| SF-268 | 16.29 | 37.03 | 102.24 | 56.01 | 104.55 |
| SF-295 | 126.17 | 109.08 | 106.36 | 91.56 | 97.26 |
| SF-539 | −47.11 | 108.52 | 106.54 | 68.26 | 107.00 |
| SNB-19 | 78.98 | 105.75 | 108.79 | 94.26 | 105.18 |
| SNB-75 | 79.03 | 85.25 | 96.12 | 39.58 | 91.73 |
| U251 | −89.26 | 29.19 | 88.75 | 30.51 | 103.69 |
| Melanoma | | | | | |
| LOX IMVI | −50.63 | 10.23 | 42 | 7.49 | 83.24 |
| MALME-3M | −71.64 | 97.09 | 106.43 | 80.81 | 105.10 |
| M14 | 74.54 | 102.73 | 106.41 | 86.54 | 105.44 |
| MDA-MB-435 | −87.88 | N.T. | N.T. | −48.29 | 106.67 |
| SK-MEL-2 | −73.16 | 0.21 | 112.49 | −3.95 | 109.49 |
| SK-MEL-28 | 15.47 | 131.75 | 127.12 | 95.00 | 130.48 |
| SK-MEL-5 | 8.52 | 72.45 | 85.68 | 22.53 | N.T. |
| UACC-257 | −83.07 | 76.09 | 92.75 | 58.86 | 95.45 |
| UACC-62 | −82.32 | 72.91 | 86.28 | 43.08 | 90.65 |
| Ovarian cancer | | | | | |
| IGROV1 | −88.34 | 52.47 | 84.4 | 43.88 | 84.93 |
| OVCAR-3 | −15.47 | 49.88 | 96.67 | 25.27 | 118.64 |
| OVCAR-4 | −94.43 | −75.03 | 57.83 | −68.15 | 76.82 |
| OVCAR-5 | −20.07 | N.T. | N.T. | N.T. | N.T. |
| OVCAR-8 | −10.07 | −4.57 | 82.3 | 6.01 | 88.60 |
| NCI/ADR-RES | −2.53 | N.T. | N.T. | 62.34 | 102.42 |
| SK-OV-3 | 100.70 | 109.05 | 105.6 | 80.29 | 108.96 |
| Renal cancer | | | | | |
| 786-0 | −25.98 | 102.14 | 110.04 | 92.60 | 108.70 |
| A498 | 130.09 | 93.79 | 95.01 | 88.61 | 93.03 |
| ACHN | −94.31 | N.T. | N.T. | N.T. | N.T. |
| CAKI-1 | 1.97 | 96.51 | 89.04 | 73.77 | 86.97 |
| RXF 393 | 20.11 | 71.92 | 114.31 | 68.12 | 117.52 |
| SN12C | −73.27 | 71.92 | 96.58 | 66.11 | 86.95 |
| TK-10 | 96.99 | 134.06 | 143.47 | 129.90 | 139.80 |
| UO-31 | −79.30 | 80.15 | 80.12 | 73.75 | 79.46 |
| Prostate cancer | | | | | |
| PC-3 | N.T. | 23.54 | 87.32 | 38.44 | 86.94 |
| DU145 | 40.76 | 96.95 | 102.73 | 82.23 | 117.15 |
| Breast cancer | | | | | |
| MCF7 | −50.74 | 65.36 | 94.88 | 56.44 | 86.11 |
| MDA-MB-231/ATCC | −17.33 | −23.35 | 66.67 | −13.36 | 89.05 |
| HS 578T | 7.40 | 72.54 | 95.89 | 59.96 | 103.37 |
| BT-549 | N.T. | 101.5 | 104.68 | 96.19 | 98.88 |
| T-47D | −45.52 | −54.59 | 93.21 | −46.11 | 85.04 |
| MDA-MB-468 | −73.17 | −88.31 | 87.29 | −85.29 | 46.13 |
| Mean | 2.68 | 54.91 | 93.48 | 51.63 | 98.08 |
| Delta | 102.68 | 143.22 | 77.74 | 136.92 | 51.95 |
| Range | 230.09 | 222.37 | 123.73 | 215.19 | 93.67 |

TABLE 3-continued

Cytotoxicity assessment of human tumor cell lines by American Institute for Cancer Screening platform

| Panel/Cell Line | Compounds | | | | |
|---|---|---|---|---|---|
| Growth Percent $^a$ (10 μM) NSC number | C10 NSC757967 | C25 NSC761881 | C27 NSC761882 | C35 NSC761883 | C37 NSC761884 |
| Leukemia | | | | | |
| CCRF-CEM | 48.31 | N.T. | N.T. | N.T. | N.T. |
| HL-60(TB) | 66.73 | 99.93 | −43.96 | 72.72 | N.T. |
| K562 | 48.27 | 67.97 | 29.66 | 47.80 | N.T. |
| MOLT-4 | 47.64 | 91.01 | 29.67 | 1.27 | N.T. |
| RPMI-8226 | 61.17 | 85.14 | 9.40 | 77.16 | N.T. |
| SR | 68.92 | 70.26 | 2.94 | 41.15 | N.T. |
| Non-small cell lung cancer | | | | | |
| A549/ATCC | 100.58 | 109.80 | 95.37 | 102.75 | 107.48 |
| EKVX | 84.52 | 108.79 | 77.74 | 109.03 | 43.65 |
| HOP-62 | 60.63 | 79.34 | 4.88 | 63.18 | 42.12 |
| HOP-92 | 90.59 | 97.83 | 37.57 | 65.12 | N.T. |
| NCI-H226 | 87.42 | 01.50 | 92.07 | 112.00 | 78.07 |
| NCI-H23 | 39.65 | 89.40 | 18.02 | 74.59 | −26.91 |
| NCI-H322M | 98.00 | N.T. | N.T. | N.T. | N.T. |
| NCI-H460 | 88.64 | 102.01 | 58.24 | 100.98 | N.T. |
| NCI-H522 | 79.03 | 96.81 | 30.77 | 91.29 | 7.18 |
| Colon cancer | | | | | |
| COLO 205 | 104.19 | 106.63 | 97.36 | 109.65 | 105.98 |
| HCC-2998 | 107.48 | 121.23 | 78.44 | 109.37 | 101.66 |
| HCT-116 | 18.89 | 94.55 | 16.62 | 81.94 | −67.84 |
| HCT-15 | 55.97 | 83.04 | 39.74 | 92.85 | 17.97 |
| HT29 | N.T. | 101.47 | 96.46 | 106.27 | 102.17 |
| KM12 | 83.91 | 96.42 | 57.85 | 101.18 | N.T. |
| CNS cancer $^b$ | | | | | |
| SF-268 | 75.83 | 90.61 | −5.11 | 82.95 | N.T. |
| SF-295 | 95.84. | N.T. | 100.07 | 78.93 | N.T. |
| SF-539 | 88.62 | 100.22 | −5.66 | 88.74 | −52.72 |
| SNB-19 | 84.82 | 102.33 | 71.38 | 84.39 | 56.88 |
| SNB-75 | 51.11 | 76.05 | 47.20 | 47.00 | 26.08 |
| U251 | 59.35 | 104.99 | 11.49 | 63.57 | −69.50 |
| Melanoma | | | | | |
| LOX IMVI | 13.57 | 90.38 | −15.34 | 73.05 | −59.25 |
| MALME-3M | 61.99 | 108.23 | 35.27 | 94.30 | −86.56 |
| M14 | 75.06 | 100.77 | 59.45 | 98.95 | −76.44 |
| MDA-MB-435 | 0.52 | 105.58 | −72.95 | 105.64 | −82.33 |
| SK-MEL-2 | 88.38 | 98.52 | 35.02 | 101.38 | −53.17 |
| SK-MEL-28 | 104.55 | 118.64 | 64.65 | 122.69 | 24.96 |
| SK-MEL-5 | 15.98 | 109.99 | 46.26 | 108.82 | 19.02 |
| UACC-257 | 79.36 | 121.93 | 4.75 | 119.38 | −84.59 |
| UACC-62 | 62.43 | 94.50 | 39.58 | 94.09 | −64.98 |
| Ovarian cancer | | | | | |
| IGROV1 | 54.88 | 95.00 | 27.94 | 78.13 | −13.50 |
| OVCAR-3 | 6.64 | 105.38 | −65.85 | 99.41 | N.T. |
| OVCAR-4 | 28.69 | N.T. | N.T. | N.T. | N.T. |
| OVCAR-5 | N.T. | 106.46 | 120.52 | 108.82 | 108.55 |
| OVCAR-8 | 43.29 | 104.59 | 2.47 | 85.13 | −22.92 |
| NCI/ADR-RES | 43.58 | 97.75 | −29.94 | 83.13 | −15.13 |
| SK-OV-3 | 104.65 | 110.36 | 66.68 | 84.09 | 95.44 |
| Renal cancer | | | | | |
| 786-0 | 109.16 | 105.11 | −6.19 | 67.49 | −2.06 |
| A498 | 88.30 | 84.37 | 24.25 | 87.70 | N.T. |
| ACHN | N.T. | 94.24 | 25.50 | 88.50 | −92.53 |
| CAKI-1 | 61.73 | N.T. | 29.67 | 108.19 | −3.69 |
| RXF 393 | 98.14 | 105.93 | −8.53 | 91.47 | −27.84 |
| SN12C | 71.73 | 98.68 | 22.56 | 96.65 | −66.17 |
| TK-10 | 131.28 | 127.11 | 76.52 | 111.76 | 53.81 |
| UO-31 | 53.93 | 65.72 | 56.15 | 91.54 | −74.79 |
| Prostate cancer | | | | | |
| PC-3 | 56.59 | 76.11 | 4.23 | 80.59 | N.T. |
| DU145 | 68.98 | 109.69 | 50.57 | 102.44 | N.T. |

TABLE 3-continued

Cytotoxicity assessment of human tumor cell lines by American Institute for Cancer Screening platform

| Breast cancer | | | | | |
|---|---|---|---|---|---|
| MCF7 | 55.12 | 79.77 | −6.39 | 85.16 | −69.36 |
| MDA-MB-231/ATCC | 39.16 | 92.27 | 16.85 | 82.44 | −29.08 |
| HS 578T | 88.35 | 99.06 | 54.25 | 72.51 | N.T. |
| BT-549 | 93.78 | 94.55 | 52.19 | 79.66 | 36.21 |
| T-47D | 60.04 | 75.36 | −33.05 | 63.44 | −42.26 |
| MDA-MB-468 | 45.59 | 100.45 | −79.88 | 90.73 | −79.19 |
| Mean | 67.97 | 97.26 | 29.61 | 87.13 | −5.75 |
| Delta | 67.45 | 31.54 | 109.49 | 85.86 | 86.78 |
| Range | 130.76 | 61.39 | 200.40 | 121.42 | 201.08 |

| Panel/Cell Line | Compounds | | | | |
|---|---|---|---|---|---|
| Growth Percent [a] (10 μM) NSC number | C39 NSC761885 | C41 NSC761886 | C43 NSC761887 | C58 NSC761888 | C46 NSC761889 |
| Leukemia | | | | | |
| CCRF-CEM | N.T. | N.T. | N.T. | N.T. | N.T. |
| HL-60(TB) | −37.71 | 102.73 | 105.25 | −40.05 | 84.53 |
| K562 | −21.06 | 91.98 | 67.50 | −23.03 | 38.52 |
| MOLT-4 | −41.57 | 82.89 | 59.93 | −41.19 | 35.83 |
| RPMI-8226 | 6.29 | 101.16 | 88.58 | −4.48 | 52.03 |
| SR | 0.20 | 101.71 | 96.31 | 0.05 | 36.14 |
| Non-small cell lung cancer | | | | | |
| A549/ATCC | 111.54 | 103.32 | 104.69 | 96.53 | 109.52 |
| EKVX | 98.12 | 148.76 | 113.82 | 97.65 | 104.94 |
| HOP-62 | 58.46 | 95.20 | 102.09 | 81.44 | 61.81 |
| HOP-92 | −18.39 | 91.38 | 04.31 | −44.56 | 100.52 |
| NCI-H226 | 88.85 | 79.51 | 79.69 | 82.43 | 95.26 |
| NCI-H23 | 9.53 | 89.13 | 81.49 | 4.86 | 76.42 |
| NCI-H322M | N.T. | N.T. | N.T. | N.T. | N.T. |
| NCI-H460 | 83.60 | 107.16 | 106.20 | 89.65 | 100.27 |
| NCI-H522 | 61.06 | 95.69 | 95.39 | 48.83 | 82.41 |
| Colon cancer | | | | | |
| COLO 205 | 104.04 | 112.25 | 117.30 | 111.91 | 109.57 |
| HCC-2998 | 107.02 | 106.85 | 111.01 | 106.02 | 104.94 |
| HCT-116 | −63.06 | 94.64 | 101.97 | −84.89 | 85.66 |
| HCT-15 | 45.84 | 109.35 | 111.56 | 82.58 | 71.89 |
| HT29 | 102.45 | 101.30 | 102.26 | 108.08 | 105.25 |
| KM12 | 51.79 | 101.28 | 100.42 | 87.50 | 97.06 |
| CNS cancer [b] | | | | | |
| SF-268 | 8.47 | 94.81 | 89.67 | 37.83 | 89.75 |
| SF-295 | 68.77 | N.T. | 98.897 | 78.47 | N.T. |
| SF-539 | 58.79 | 93.53 | 96.48 | 93.92 | 107.05 |
| SNB-19 | 87.35 | 113.97 | 101.61 | 103.09 | 105.92 |
| SNB-75 | 42.86 | 79.05 | 75.08 | 70.82 | 81.80 |
| U251 | 34.47 | 102.73 | 103.89 | 43.78 | 100.67 |
| Melanoma | | | | | |
| LOX IMVI | −42.03 | 90.24 | 68.98 | −54.85 | 70.96 |
| MALME-3M | 39.46 | 89.52 | 104.58 | 18.08 | 113.06 |
| M14 | 53.77 | 92.89 | 107.55 | 73.52 | 94.23 |
| MDA-MB-435 | −85.27 | 118.61 | 118.40 | −80.50 | 72.50 |
| SK-MEL-2 | 51.79 | 99.24 | 89.27 | 14.45 | 82.62 |
| SK-MEL-28 | 79.45 | 115.63 | 119.66 | 108.55 | 101.77 |
| SK-MEL-5 | 48.53 | 106.14 | 101.45 | 61.76 | 100.11 |
| UACC-257 | 43.93 | 118.11 | 109.51 | −10.49 | 104/27 |
| UACC-62 | 53.27 | 108.99 | 110.99 | 69.46 | 87.72 |
| Ovarian cancer | | | | | |
| IGROV1 | 975 | 103.17 | 95.67 | −30.93 | 99.91 |
| OVCAR-3 | −52.32 | 109.57 | 102.89 | −90.05 | 85.83 |
| OVCAR-4 | N.T. | N.T. | N.T. | N.T. | N.T. |
| OVCAR-5 | 110.21 | 103.00 | 108.31 | 118.16 | 122.58 |
| OVCAR-8 | 0.32 | 99.50 | 97.37 | 18.67 | 97.32 |
| NCI/ADR-RES | −26.24 | 97.60 | 91.79 | 37.25 | 92.67 |
| SK-OV-3 | 92.58 | 106.18 | 102.46 | 115.11 | 110.30 |
| Renal cancer | | | | | |
| 786-0 | 3.74 | 94.93 | 109.83 | −96.82 | 102.97 |
| A498 | 50.80 | 84.77 | 56.04 | 68.74 | 83.74 |
| ACHN | 34.93 | 102.26 | 103.64 | −71.76 | 98.70 |

TABLE 3-continued

Cytotoxicity assessment of human tumor cell lines by American Institute for Cancer Screening platform

| | | | | | |
|---|---|---|---|---|---|
| CAKI-1 | 24.02 | 108.29 | 99.44 | 59.22 | N.T. |
| RXF 393 | 36.69 | 109.28 | 106.98 | 60.19 | 124.15 |
| SN12C | 9.12 | 106.54 | 98.04 | 77.39 | 95.93 |
| TK-10 | 111.93 | 135.79 | 128.10 | 80.94 | 130.80 |
| UO-31 | 70.30 | 68.31 | 67.56 | −79.21 | 75.49 |
| Prostate cancer | | | | | |
| PC-3 | −9.72 | 82.81 | 78.37 | 14.77 | 75.99 |
| DU145 | 41.32 | 112.48 | 101.05 | 58.15 | 98.87 |
| Breast cancer | | | | | |
| MCF7 | 6.58 | 93.78 | 82.87 | 68.59 | 72.77 |
| MDA-MB-231/ATCC | −9.73 | 87.58 | 78.80 | 4.55 | 87.08 |
| HS 578T | 50.08 | 96.71 | 96.47 | N.T. | 93.84 |
| BT-549 | 66.40- | 92.92 | 107.82 | 76.58 | 94.91 |
| T-47D | −28.61 | 89.66 | 86.56 | −52.85 | 69.09 |
| MDA-MB-468 | −86.96 | 112.95 | 82.25 | −80.08 | 93.53 |
| Mean | 32.54 | 1000.77 | 96.80 | 28.56 | 91.30 |
| Delta | 119.50 | 32.46 | 40.76 | 125.38 | 55.47 |
| Range | 198.89 | 80.45 | 72.06 | 214.98 | 94.97 |

| Panel/Cell Line | Compounds | | | | |
|---|---|---|---|---|---|
| Growth Percent $^a$ (10 μM) | C48 | C42 | C50 | C15 | C60 |
| NSC number | NSC761890 | NSC761891 | NSC761892 | NSC763952 | NSC763953 |
| Leukemia | | | | | |
| CCRF-CEM | N.T. | N.T. | N.T. | 43.60 | 44.80 |
| HL-60(TB) | −79.53 | 73.6 | N.T. | 51.57 | 23.13 |
| K562 | 32.30 | 75.57 | N.T. | 59.58 | 32.82 |
| MOLT-4 | 67.31 | 71.40 | N.T. | 42.86 | 11.82 |
| RPMI-8226 | 48.56 | 89.13 | N.T. | 56.96 | 36.51 |
| SR | 23.00 | 78.44 | N.T. | 55.02 | 19.52 |
| Non-small cell lung cancer | | | | | |
| A549/ATCC | 104.68 | 107.23 | 111.48 | 62.74 | 72.79 |
| EKVX | 104.56 | 100.45 | 102.26 | 86.63 | 81.16 |
| HOP-62 | 59.51 | 90.96 | 91.94 | 76.66 | 71.23 |
| HOP-92 | 89.91 | 93.51 | N.T. | N.T. | 88.03 |
| NCI-H226 | 95.71 | 87.97 | 90.47 | 78.10 | 66.43 |
| NCI-H23 | 53.21 | 90.39 | 94.07 | 33.45 | 58.67 |
| NCI-H322M | N.T. | N.T. | N.T. | 91.69 | 91.20 |
| NCI-H460 | 88.86 | 104.64 | N.T. | 87.46 | 29.27 |
| NCI-H522 | 74.81 | 105.78 | 98.19 | 38.70 | 49.77 |
| Colon cancer | | | | | |
| COLO 205 | 99.23 | 106.04 | 106.49 | 107.31 | 94.87 |
| HCC-2998 | 124.00 | 108.80 | 105.49 | 107.83 | 91.26 |
| HCT-116 | 92.15 | 92.29 | 100.93 | 88.21 | 40.51 |
| HCT-15 | 38.57 | 90.91 | 103.08 | 61.93 | 37.73 |
| HT29 | 104.31 | 104.91 | 106.40 | 86.91 | 91.07 |
| KM12 | 103.11 | 105.36 | N.T. | 83.12 | 71.40 |
| CNS cancer $^b$ | | | | | |
| SF-268 | 74.73 | 108.19 | N.T. | 95.90 | 63.91 |
| SF-295 | 104.92 | 91.11 | N.T. | 94.85 | 78.76 |
| SF-539 | 78.04 | 94.94 | 93.72 | 90.64 | 69.85 |
| SNB-19 | 103.54 | 106.60 | 103.22 | 100.15 | 87.03 |
| SNB-75 | 76.30 | 80.61 | 77.25 | 105.73 | 69.41 |
| U251 | 62.36 | 107.58 | 109.69 | 40.24 | 35.47 |
| Melanoma | | | | | |
| LOX IMVI | 30.01 | 90.18 | 84.11 | 30.16 | 27.09 |
| MALME-3M | 96.77 | 101.93 | 108.70 | 48.56 | 61.29 |
| M14 | 94.25 | 100.28 | 103.80 | 117.70 | 106.75 |
| MDA-MB-435 | 80.61 | 104.60 | 106.07 | 77.03 | 72.21 |
| SK-MEL-2 | 73.29 | 107.90 | 102.98 | 43.98 | 84.09 |
| SK-MEL-28 | 105.73 | 111.81 | 112.20 | 90.60 | 77.13 |
| SK-MEL-5 | 87.54 | 107.45 | 106.82 | 22.81 | 29.92 |
| UACC-257 | 87.32 | 115.60 | 126.28 | 35.78 | 69.64 |
| UACC-62 | 90.69 | 102.82 | 108.85 | 83.96 | 64.65 |
| Ovarian cancer | | | | | |
| IGROV1 | 80.06 | 96.70 | 94.67 | 75.28 | 55.18 |
| OVCAR-3 | 5.30 | 118.49 | N.T. | 41.52 | 76.23 |
| OVCAR-4 | N.T. | N.T | N.T. | 0.28 | 9.58 |

TABLE 3-continued

Cytotoxicity assessment of human tumor cell lines by American Institute for Cancer Screening platform

| | | | | | |
|---|---|---|---|---|---|
| OVCAR-5 | 126.28 | 107.20 | 116.60 | 112.62 | 121.21 |
| OVCAR-8 | 76.29 | 92.19 | 112.41 | 41.72 | 45.71 |
| NCI/ADR-RES | 59.53 | 97.53 | 101.92 | 54.16 | 55.91 |
| SK-OV-3 | 93.79 | 97.49 | 99.36 | N.T. | N.T. |
| Renal cancer | | | | | |
| 786-0 | 100.36 | 98.25 | 100.25 | 120.26 | 95.95 |
| A498 | 85.54 | 93.56 | N.T. | N.T. | N.T. |
| ACHN | 89.76 | 98.02 | 103.33 | 83.52 | 70.10 |
| CAKI-1 | 81.47 | 91.05 | 84.23 | 76.06 | 58.59 |
| RXF 393 | 95.88 | 112.19 | 118.35 | 85.93 | 66.60 |
| SN12C | 85.97 | 104.90 | 104.76 | 76.76 | 81.98 |
| TK-10 | 122.97 | 131.58 | 125.26 | 106.46 | 100.37 |
| UO-31 | 62.14 | 69.14 | 76.69 | 61.00 | 49.04 |
| Prostate cancer | | | | | |
| PC-3 | 73.26 | 81.30 | N.T. | 56.99 | 42.48 |
| DU145 | 101.53 | 122.43 | N.T. | 79.83 | 87.28 |
| Breast cancer | | | | | |
| MCF7 | 66.12 | 75.84 | 78.81 | 49.73 | 59.01 |
| MDA-MB-231/ATCC | 60.72 | 99.22 | 100.81 | 45.69 | 57.00 |
| HS 578T | 83.69 | 104.51 | N.T. | 84.36 | 76.50 |
| BT-549 | 95.35 | 95.06 | 103.88 | 104.74 | 96.78 |
| T-47D | 51.89 | 81.07 | 86.51 | 56.78 | 65.23 |
| MDA-MB-468 | 53.68 | 116.25 | 108.00 | 12.59 | 32.52 |
| Mean | 80.61 | 98.32 | 101.69 | 70.31 | 63.19 |
| Delta | 75.31 | 29.18 | 25.00 | 70.03 | 53.61 |
| Range | 120.98 | 62.44 | 49.59 | 119.98 | 111.63 |

| Panel/Cell Line | Compounds | | | | |
|---|---|---|---|---|---|
| Growth Percent[a] (10 µM) NSC number | C65 NSC761890 | C55 NSC761891 | C56 NSC761892 | C16 NSC763952 | C61 NSC763953 |
| Leukemia | | | | | |
| CCRF-CEM | 29.84 | 34.84 | N.T. | −35.53 | 17.83 |
| HL-60(TB) | 8.17 | 47.83 | 57.42 | −45.01 | 1.11 |
| K562 | 35.29 | 43.14 | 67.53 | −44.64 | 16.97 |
| MOLT-4 | 20.18 | 32.64 | 22.72 | −50.44 | −11.92 |
| RPMI-8226 | 40.73 | 55.63 | 86.78 | −35.20 | 16.20 |
| SR | 23.58 | 35.52 | 63.73 | −54.27 | −15.27 |
| Non-small cell lung cancer | | | | | |
| A549/ATCC | 69.22 | 90.16 | 100.62 | 20.39 | 27.13 |
| EKVX | 80.90 | 82.44 | N.T. | 56.13 | 62.56 |
| HOP-62 | 79.67 | 90.01 | 89.15 | 2.44 | 40.78 |
| HOP-92 | N.T. | N.T. | N.T. | N.T. | N.T. |
| NCI-H226 | 74.35 | 78.31 | 82.14 | 53.41 | 47.00 |
| NCI-H23 | 53.59 | 67.37 | 82.13 | −25.43 | 37.57 |
| NCI-H322M | 91.66 | 83.83 | 94.10 | 89.71 | 64.54 |
| NCI-H460 | 81.55 | 87.37 | 104.55 | 27.92 | 11.85 |
| NCI-H522 | 47.67 | 61.39 | 82.61 | −88.01 | 12.41 |
| Colon cancer | | | | | |
| COLO 205 | 90.97 | 98.76 | 99.94 | 97.05 | 83.39 |
| HCC-2998 | 97.85 | 100.96 | 102.54 | 90.47 | 57.61 |
| HCT-116 | 52.51 | 64.99 | 114.73 | −82.82 | 24.23 |
| HCT-15 | 45.61 | 47.54 | 97.91 | 2.65 | 28.74 |
| HT29 | 98.33 | 97.73 | 96.41 | 77.39 | 52.64 |
| KM12 | 83.42 | 95.96 | 105.46 | 69.33 | 40.14 |
| CNS cancer[b] | | | | | |
| SF-268 | 69.25 | 79.48 | 107.19 | −54.89 | 39.57 |
| SF-295 | 86.04 | 91.11 | N.T. | 79.94 | 34.71 |
| SF-539 | 75.99 | 84.51 | 97.95 | −22.78 | 47.90 |
| SNB-19 | 94.57 | 94.75 | 104.30 | 83.19 | 61.89 |
| SNB-75 | 83.19 | 69.38 | 63.35 | 33.65 | 43.18 |
| U251 | 43.08 | 53.94 | 94.44 | −73.58 | 19.18 |
| Melanoma | | | | | |
| LOX IMVI | 29.97 | 44.61 | 86.69 | −91.42 | 8.17 |
| MALME-3M | 58.74 | 73.72 | 86.38 | −58.68 | 64.72 |
| M14 | 118.36 | 121.55 | 126.40 | 47.15 | 61.89 |
| MDA-MB-435 | 27.37 | 96.77 | N.T. | −61.08 | N.T. |
| SK-MEL-2 | 72.52 | 67.54 | 109.63 | −69.35 | 32.64 |

TABLE 3-continued

Cytotoxicity assessment of human tumor cell lines by American Institute for Cancer Screening platform

| | | | | | |
|---|---|---|---|---|---|
| SK-MEL-28 | 87.69 | 89.33 | 95.35 | −41.99 | 53.13 |
| SK-MEL-5 | 49.49 | 70.23 | 89.57 | −94.86 | 8.03 |
| UACC-257 | 50.45 | 86.57 | 78.70 | −86.35 | 33.79 |
| UACC-62 | 85.80 | 91.72 | 101.52 | −38.24 | 57.68 |
| Ovarian cancer | | | | | |
| IGROV1 | 69.50 | 66.38 | 84.25 | −54.45 | 25.29 |
| OVCAR-3 | 10.25 | 1.00 | 113.46 | −76.39 | 22.37 |
| OVCAR-4 | −4.36 | 4.00 | 84.19 | −100.00 | −5.69 |
| OVCAR-5 | 114.60 | 113.96 | 104.48 | 115.03 | 79.06 |
| OVCAR-8 | 36.77 | 58.98 | 94.19 | −79.84 | 22.87 |
| NCI/ADR-RES | 48.31 | 59.68 | 95.73 | −37.28 | 28.36 |
| SK-OV-3 | N.T. | N.T. | N.T. | N.T. | N.T. |
| Renal cancer | | | | | |
| 786-0 | 114.97 | 115.19 | 117.98 | 80.27 | 63.62 |
| A498 | N.T. | N.T. | N.T. | N.T. | N.T. |
| ACHN | 74.11 | 83.18 | 94.35 | −44.97 | 38.07 |
| CAKI-1 | 72.65 | 61.03 | N.T. | −1.76 | 27.55 |
| RXF 393 | 66.49 | 76.16 | 104.79 | −62.42 | 45.35 |
| SN12C | 86.43 | 67.67 | 93.61 | −61.79 | 46.94 |
| TK-10 | 110.93 | 119.41 | 121.91 | 103.17 | 63.75 |
| UO-31 | 61.81 | 66.73 | 68.47 | −58.89 | 17.74 |
| Prostate cancer | | | | | |
| PC-3 | 44.52 | 59.94 | 82.91 | −19.24 | 35.60 |
| DU145 | 74.73 | 106.29 | 115.38 | 21.90 | 47.51 |
| Breast cancer | | | | | |
| MCF7 | 63.15 | 68.59 | 82.97 | −72.70 | 22.53 |
| MDA-MB-231/ATCC | 35.85 | 30.57 | 95.23 | −56.83 | 31.45 |
| HS 578T | 85.89 | 82.43 | 88.59 | −3.91 | 72.44 |
| BT-549 | 98.07 | 105.06 | 115.07 | 83.33 | 75.04 |
| T-47D | 51.78 | 66.81 | 83.77 | −59.61 | 45.05 |
| MDA-MB-468 | 14.40 | 45.85 | 83.39 | −99.82 | 12.85 |
| Mean | 63.92 | 73.30 | 92.68 | −15.40 | 36.29 |
| Delta | 68.28 | 72.30 | 69.96 | 84.60 | 51.56 |
| Range | 122.72 | 120.55 | 103.68 | 215.03 | 98.66 |

| Panel/Cell Line | Compounds | | | |
|---|---|---|---|---|
| Growth Percent [a] (10 μM) NSC number | C64 NSC764965 | C7 NSC763966 | C8 NSC763967 | C18 NSC763968 |
| Leukemia | | | | |
| CCRF-CEM | 59.59 | 86.62 | −12.55 | −45.05 |
| HL-60(TB) | 46.13 | 104.58 | −10.38 | −41.24 |
| K562 | 33.45 | 75.50 | −24.44 | −26.17 |
| MOLT-4 | 12.86 | 92.84 | −41.28 | −54.56 |
| RPMI-8226 | 21.59 | 76.16 | −29.81 | −38.03 |
| SR | 26.12 | 84.23 | −49.98 | −47.97 |
| Non-small cell lung cancer | | | | |
| A549/ATCC | 56.25 | 63.51 | −60.09 | −8.14 |
| EKVX | 82.17 | 75.67 | −25.35 | −6.58 |
| HOP-62 | 65.10 | 79.16 | −67.97 | 13.18 |
| HOP-92 | N.T. | N.T. | −25.30 | N.T. |
| NCI-H226 | 66.61 | 78.66 | 69.78 | 10.21 |
| NCI-H23 | 45.87 | 59.74 | −43.43 | −42.19 |
| NCI-H322M | 94.85 | 82.34 | −56.32 | −0.80 |
| NCI-H460 | 21.80 | 89.11 | −38.31 | 4.92 |
| NCI-H522 | 53.06 | 83.41 | −91.81 | −59.54 |
| Colon cancer | | | | |
| COLO 205 | 100.68 | 82.13 | −99.38 | 102.47 |
| HCC-2998 | 95.82 | 104.58 | −86.18 | 21.00 |
| HCT-116 | 31.32 | 78.67 | −2.07 | −36.70 |
| HCT-15 | 32.24 | 61.25 | −60.44 | 15.31 |
| HT29 | 96.29 | 98.60 | −45.50 | 48.08 |
| KM12 | 64.56 | 95.18 | −21.66 | 19.33 |
| CNS cancer [b] | | | | |
| SF-268 | 52.27 | 98.43 | −14.54 | 7.06 |
| SF-295 | 75.76 | 87.02 | −55.73 | −16.57 |
| SF-539 | 70.48 | 97.27 | −82.05 | −47.01 |
| SNB-19 | 82.28 | 90.45 | −77.31 | 21.85 |

TABLE 3-continued

Cytotoxicity assessment of human tumor cell lines by American Institute for Cancer Screening platform

| | | | | |
|---|---|---|---|---|
| SNB-75 | 80.91 | 94.52 | −73.34 | 9.12 |
| U251 | 34.17 | 80.49 | −55.42 | −23.10 |
| Melanoma | | | | |
| LOX IMVI | 27.05 | 69.55 | −90.91 | −21.59 |
| MALME-3M | 78.41 | 70.73 | −85.22 | −86.04 |
| M14 | 76.72 | 94.61 | −96.08 | −31.54 |
| MDA-MB-435 | 65.53 | 105.87 | −58.82 | −79.28 |
| SK-MEL-2 | 93.85 | 115.43 | −66.52 | −55.62 |
| SK-MEL-28 | 74.97 | 99.46 | −50.60 | −8.32 |
| SK-MEL-5 | 24.13 | 31.12 | −98.79 | −99.20 |
| UACC-257 | 71.17 | 84.14 | −88.80 | −91.69 |
| UACC-62 | 67.41 | 95.64 | −47.85 | −57.09 |
| Ovarian cancer | | | | |
| IGROV1 | 49.40 | 75.83 | −28.40 | −32.91 |
| OVCAR-3 | 57.92 | 86.97 | −38.62 | −60.32 |
| OVCAR-4 | 31.44 | 77.50 | −71.27 | −100.00 |
| OVCAR-5 | 109.85 | 111.75 | −76.97 | −27.85 |
| OVCAR-8 | 53.96 | 82.12 | −28.91 | −22.64 |
| NCI/ADR-RES | 61.34 | 86.36 | −23.20 | −24.93 |
| SK-OV-3 | N.T. | N.T. | N.T. | N.T. |
| Renal cancer | | | | |
| 786-0 | 74.18 | 96.67 | −14.05 | 12.37 |
| A498 | N.T. | N.T. | N.T. | N.T. |
| ACHN | 57.60 | 82.97 | −22.86 | 0.80 |
| CAKI-1 | 50.33 | 70.65 | 6.88 | −5.68 |
| RXF 393 | 71.05 | 97.02 | −59.58 | 13.64 |
| SN12C | 74.58 | 89.82 | −95.78 | −28.62 |
| TK-10 | 95.15 | 141.01 | −35.59 | 30.33 |
| UO-31 | 56.97 | 41.64 | −28.47 | −28.43 |
| Prostate cancer | | | | |
| PC-3 | 45.73 | 71.01 | −18.35 | −13.43 |
| DU145 | 68.26 | 105.08 | −95.45 | 6.66 |
| Breast cancer | | | | |
| MCF7 | 46.59 | 59.71 | −49.41 | −68.82 |
| MDA-MB-231/ATCC | 73.83 | 95.23 | −2.96 | −35.94 |
| HS 578T | 78.75 | 101.62 | 4.32 | −9.16 |
| BT-549 | 76.36 | 86.83 | −99.43 | 10.84 |
| T-47D | 64.48 | 78.19 | 12.90 | −24.37 |
| MDA-MB-468 | 58.18 | 84.32 | −62.81 | −78.76 |
| Mean | 61.35 | 85.69 | −49.52 | −21.64 |
| Delta | 48.49 | 54.57 | 49.51 | 78.36 |
| Range | 96.99 | 109.89 | 112.33 | 202.47 |

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A heterocyclic fused anthraquinone derivative, which is represented by a formula (I):

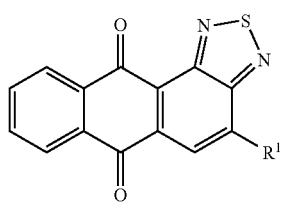

wherein $R^1$ is sulfoalkyl group, piperazino group, amino-cyclopentylamino group, amino-butylamino group, amino-ethylamino, amino-2-methylpropylamino group, oxide potassium or one substituent represented by a formula (II):

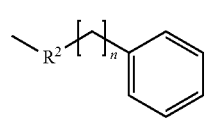

wherein $R^2$ is, oxyl group or a thiol group, and the one or more hydrogens of the phenyl group represented by a formula (II) can be substituted by halogen, alkoxy group, nitro group, methylthio group or sulfhydryl, wherein when $R^2$ is oxyl group then n is 0, and when n is thiol group then n is 0-2, wherein when $R^1$ is sulfoalkyl group, wherein the alkyl group is selected from the group consisting of $C_{1-10}$ straight-chain alkyl group, $C_{3-10}$ branched alkyl group and $C_{3-10}$ cyclic alkyl group, wherein when the $R^2$ is sulfur group, $R^1$ is 2,5-dimethylphenylthio group, benzylthio group, 4-chlorophenylthio group, 2,4-dimethylphenylthio group, 4-isopropylphenylthio group, 4-fluorophenylthio group, phenylthioethyl group, 2,3-dichlorophenylthio group, 4-tert-butylphenylthio group, 2-chlorophenylthio group, 2-fluorophenylthio group, 2,5-dichlorophenylthio group, 2-thiolphenylthio, 3-chlorophenylthio, 3-fluorophenylthio group, 2,4-difluorophenylthio group, 3,4-dimethylphenylthio group, 4-methylthiophenylthio group, 4-nitrophenylthio group, 3-methoxyphenylthio group, meta-benzylthio group, ortho-benzylthio group, 3,5-dimethylphenylthio group, 3-ethoxyphenylthio group, 2-ethylphenylthio group, 2-isopropylphenylthio group, 2,6-diethylphenylthio group 4-chlorobenzylthio group or 4-tert-butyl benzylthio group.

2. The heterocyclic fused anthraquinone derivative of claim 1, wherein $R^1$ is oxide potassium, ethyl piperazino group, thio-morpholino group, thio-ethyl group, thio-n-propyl group or thio-isopropyl group.

3. The heterocyclic fused anthraquinone derivative of claim 1, wherein the $R^2$ is oxygen and $R^1$ is para-methylphenyl-oxy group.

4. A pharmaceutical composition for treating cancer, which comprises a thiazole fused anthraquinone derivative or the pharmaceutical acceptable salt and carrier thereof:

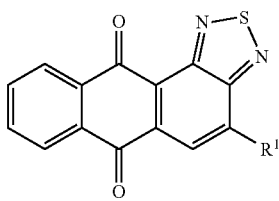

(I)

wherein $R^1$ is piperazino group, amino-cyclopentylamino group, amino-butylamino group, amino-ethylamino, amino-2-methylpropylamino group or one substituent represented by a formula (II):

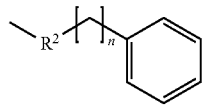

(II)

wherein $R^2$ is oxyl group or a thiol group, and one or more hydrogens of benzene in formula II can be substituted by halogen, alkoxy group, nitro group, methylthio group or sulfhydryl, wherein when $R^2$ is oxyl group then n is 0, and when n is thiol group then n is 0-2, wherein when the $R^2$ is sulfur group, $R^1$ is 2,5-dimethylphenylthio group, benzylthio group, 4-chlorophenylthio group, 2,4-dimethylphenylthio group, 4-isopropylphenylthio group, 4-fluorophenylthio group, phenylthioethyl group, 2,3-dichlorophenylthio group, 2-chlorophenylthio group, 2-fluorophenylthio group, 2,5-dichlorophenylthio group, 2-thiolphenylthio, 3-chlorophenylthio, 3-fluorophenylthio group, 2,4-difluorophenylthio group, 3,4-dimethylphenylthio group, 4-methylthiophenylthio group, 4-nitrophenylthio group, 3-methoxyphenylthio group, meta-benzylthio group, ortho-benzylthio group, 3,5-dimethylphenylthio group, 3-ethoxyphenylthio group, 2-ethylphenylthio group, 2-isopropylphenylthio group, 2,6-diethylphenylthio group, 4-chlorobenzylthio group or 4-tert-butyl benzylthio group.

5. The pharmaceutical composition of claim 4, wherein $R^1$ is oxide potassium, ethyl piperazino group, thio-morpholino group, thio-ethyl group, thio-n-propyl group or thio-isopropyl group.

6. The pharmaceutical composition of claim 4, wherein the $R^2$ is oxygen and $R^1$ is para-methylphenyl-oxy group.

7. The pharmaceutical composition of claim 4, wherein the pharmaceutical acceptable salt is a physiological acceptable inorganic acid, organic acid or base, wherein the inorganic acid can be selected from the group consisting of HCl, HBr, $H_2SO_4$, sulfonic acid and $H_2PO_3$, wherein the organic salt can be selected from the group consisting of citric acid, acetic acid, maleic acid, fumaric acid, gluconic acid, glycolic acid, methanesulfonic acid, succinic acid and galactose.

8. The pharmaceutical composition of claim 4, wherein the carrier is an excipient agent, diluting agent, thickening agent, bulking agent, binder, disintegrating agent, lubricating agent, oil or non-oil based agent, surfactant, suspending agent, gelating agent, supporting agent, preservative agent, antioxidative agent, stabilizing agent, coloring agent or fragrance.

9. The pharmaceutical composition of claim 8, wherein the excipient agent includes microcrystalline cellulose, polyvinylpyrrolidone, corn starch, modified starch, carboxymethyl starch sodium, polystyrene, gelatinized starch, sugar, polyethylene glycol, polyvinyl alcohol, hypromellose, carboxymethyl cellulose, hydroxymethylcellulose or hydroxypropyl methylcellulose.

10. The pharmaceutical composition of claim 4, which is used as a pharmaceutical composition inhibiting a non-adenosine telomerase.

11. The pharmaceutical composition of claim 4, which is a powder, a granule, a liquid, a gel or a paste.

12. The pharmaceutical composition of claim 4, which is administered by oral intake, epidermal absorption, injection or inhalation.

* * * * *